(12) United States Patent
De Both et al.

(10) Patent No.: US 9,518,258 B2
(45) Date of Patent: Dec. 13, 2016

(54) TARGETED ALTERATION OF DNA WITH OLIGONUCLEOTIDES

(75) Inventors: Michiel Theodoor Jan De Both, Wageningen (NL); Tomoyuki Furukawa, Wageningen (NL)

(73) Assignee: KEYGENE N.V., Wageningen (NL)

( * ) Notice: Subject to any disclaimer, the term of this patent is extended or adjusted under 35 U.S.C. 154(b) by 435 days.

(21) Appl. No.: 13/991,065

(22) PCT Filed: Nov. 25, 2011

(86) PCT No.: PCT/NL2011/050805
§ 371 (c)(1),
(2), (4) Date: Aug. 16, 2013

(87) PCT Pub. No.: WO2012/074386
PCT Pub. Date: Jun. 7, 2012

(65) Prior Publication Data
US 2013/0330774 A1   Dec. 12, 2013

Related U.S. Application Data

(60) Provisional application No. 61/419,183, filed on Dec. 2, 2010.

(51) Int. Cl.
*C12N 15/00* (2006.01)
*C12N 15/10* (2006.01)

(52) U.S. Cl.
CPC ......... *C12N 15/1024* (2013.01); *C12N 15/102* (2013.01); *C12N 15/1082* (2013.01)

(58) Field of Classification Search
None
See application file for complete search history.

(56) References Cited

U.S. PATENT DOCUMENTS

| | | | |
|---|---|---|---|
| 5,594,121 A | 1/1997 | Froehler et al. | |
| 5,795,972 A | 8/1998 | Kmiec | |
| 6,043,060 A | 3/2000 | Imanishi | |
| 6,136,601 A | 10/2000 | Meyer, Jr. et al. | |
| 6,268,490 B1 | 7/2001 | Imanishi et al. | |
| 6,936,467 B2 | 8/2005 | Kmiec et al. | |
| 7,226,785 B2 | 6/2007 | Kmiec et al. | |
| 2003/0163849 A1 | 8/2003 | May et al. | |
| 2003/0236208 A1 | 12/2003 | Kmiec et al. | |

FOREIGN PATENT DOCUMENTS

| | | |
|---|---|---|
| WO | WO 98/39352 A1 | 11/1998 |
| WO | WO 99/14226 A2 | 3/1999 |
| WO | WO 99/58702 A1 | 11/1999 |
| WO | WO 00/56748 A1 | 9/2000 |
| WO | WO 00/66604 A2 | 11/2000 |
| WO | WO 01/87914 A2 | 11/2000 |
| WO | WO 01/73002 A2 | 10/2001 |
| WO | WO 01/92512 A2 | 12/2001 |
| WO | WO 02/26967 A2 | 4/2002 |
| WO | WO 03/013226 A2 | 2/2003 |
| WO | WO 03/027265 A2 | 4/2003 |
| WO | WO 2007/073154 A1 | 5/2007 |
| WO | WO 2007/073149 A1 | 6/2007 |
| WO | WO 2010/017932 A1 | 2/2010 |
| WO | WO 2012/074385 A1 | 6/2012 |

OTHER PUBLICATIONS

Urban et al. A rapid and efficient method for site-directed mutagenesis using one-step overlap extension PCR. Nucleic Acids Res. (1997) vol. 25, No. 11, pp. 2227-2228.*
Nassal et al. PCR-based site-directed mutagenesis using primers with mismatched 3'-ends. Nucleic Acids Res. (1990) vol. 18, No. 10, pp. 3077-3078.*
Stoynova et al. Generation of large deletion mutants from plasmid DNA. BioTechniques (2004) vol. 36, No. 3, pp. 402-406.*
Alexeev, V. and Yoon, K. (1998). Stable and inheritable changes in genotype and phenotype of albino melanocytes induced by an RNA-DNA oligonucleotide. Nat Biotechnol 16, 1343-6.
Beetham, P. R., Kipp, P. B., Sawycky, X. L., Arntzen, C. J. and May, G. D. (1999). A tool for functional plant genomics: chimeric RNA/DNA oligonucleotides cause in vivo gene-specific mutations. Proc Natl Acad Sci USA 96, 8774-8.
Dong, C., Beetham. P., Vincent, K. and Sharp, P. (2006). Oligonucleotide-directed gene repair in wheat using a transient plasmid gene repair assay system. Plant Cell Rep 25, 457-65.
Igoucheva, O., Alexeev, V. and Yoon. K. (2001). Targeted gene correction by small single-stranded oligonucleotides in mammalian cells. Gene Ther 8, 391-9.
Kmiec, E. B. (2003). Targeted gene repair—in the arena. J Clin Invest 112, 632-6.
Kochevenko, A. and Willmitzer, L. (2003), Chimeric RNA/DNA oligonucleotide-dased site-specific modification of the tobacco acetolactate syntase gene. Plant Physiol 132, 174-84.

(Continued)

*Primary Examiner* — David Thomas

(74) *Attorney, Agent, or Firm* — Finnegan, Henderson, Farabow, Garrett & Dunner, L.L.P.

(57) ABSTRACT

The current invention relates to a method for targeted alteration of acceptor DNA, for example duplex acceptor DNA. The method comprises use of at least two oligonucleotides, each oligonucleotide having at least one mismatch relative to the targeted (duplex) acceptor DNA. The mismatch of the first oligonucleotide is directed to a nucleotide at a position in the first strand of the duplex and the mismatch of the second oligonucleotide is directed to the nucleotide in the second strand that occupies the complementary position in the duplex acceptor DNA (e.g. forms a base-pair with the nucleotide in the first strand). These mismatches are located at specific positions within said oligonucleotides. Also provided is a kit that comprises instructions for performing the method according to the inventions, and in a preferred embodiment, comprises oligonucleotides suitable for use in the method.

25 Claims, 7 Drawing Sheets

(56) References Cited

OTHER PUBLICATIONS

Liu, L., Cheng, S., van Brabant, A. J. and Kmiec, E. B. (2002). Rad51p and Rad54p, but not Rad52p, elevate gene repair in Saccharomyces cerevisiae directed by modified single-stranded oligonucleotide vectors. Nucleic Acids Res 30 2742-50.

Okuzaki, A. and Toriyama, K. (2004). Chimeric RNA/DNA oligonucleotide-directed gene targeting in rice. Plant Cell Rep 22. 509-12.

Parekh-Olmedo, H., Ferrara, L., Brachman, E. and Kmiec, E. B. (2005). Gene therapy progress and prospects, targeted gene repair. Gene Ther 12, 639-46.

Rice, M. C., Czymmek, K. and Kmiec, E. B. (2001). The potential of nucleic acid repair in functional genomics. Nat Biotechnol 19, 321-6.

Ruiter, R., van den Brande, I., Stals, E., Delaure, S., Cornelissen, M. and D'Halluin, K. (2003) Spontaneous mutation frequency in plants obscures the effect of chimeraplasty. Plant Mol Biol 53, 675-89.

Shahin, E. A. (1985). Totipotency of tomato protoplasts. Theor. Appl. Genet. 69, 235-240.

Tan, M.-L, M. C., Colijn-Hooymans, C. M., Lindhout, W. H. and Kool, A. J. (1987a). A comparison of shoot regeneration from protoplasts and leaf discs of different genotypes of the cultivated tomato, Theor. Appl. Genet. 75, 105-108.

Tan, M.-L, M. C., Rietveld, E. M., van Marrewijk, G. A. M. and Kool, A. J. (1987b). Regeneration of leaf mesophyll protoplasts of tomato cultivars (*L. esculentum*): factors important for efficient protoplast culture and regeneration. Plant Cell Reports 6, 172-175.

Zhu, T., Mettenburg, K., Peterson, D. J., Tagliani, L., and Baszczynski, C. L. (2000), Engineering herbicide-resistant maize using chimeric RNA/DNA oligonucleotides. Nat Biotechnol 18, 555-8.

Zhu, T., Peterson, D. J., Tagliani, L., St. Clair, G., Baszczynski, C. L. and Bowen, B. (1999). Targeted manipulation of maize genes in vivo using chimeric RNA/DNA oligonucleotides. Proc Natl Acad Sci USA 96, 8768-73.

First Office Action issued in corresponding Chinese patent application No. 201180066401.1, dated Jul. 7, 2014.

Search Report and Written Opinion for Netherlands Application No. 2005809 dated Jul. 1, 2011.

Andrieu-Soler et al. (2005). Stable transmission of targeted gene modification using single-stranded oligonucleotides with flanking LNAs. Nucleic Acids Research 33, No. 12, 3733-42.

Olsen et al. (2005). Genomic sequence correction by single-stranded DNA oligonucleotides: role of DNA synthesis and chemical modifications of the oligonucleotide ends. J Gene Med 7, 1534-44.

* cited by examiner

Figure 1.

```
  1    ATGGGAAGAG GATCGCATCA CCACCATCAT CATAAGCTTC CAAAGAAGAA GAGGAAGGT
 60    TCTCGAGATG GTGAGCAAGG GCTAGGAGCT GTTCACCGGG GTGGTGCCCA TCCTGGTCG
120    AGCTGGACGG CGACGTAAAC GGCCACAAGT TCAGCGTGTC CGGCGAGGGC GAGGGCGAT
180    GCCACCTACG GCAAGCTGAC CCTGAAGTTC ATCTGCACCA CCGGCAAGCT GCCCGTGCC
240    CTGGCCCACC CTCGTGACCA CCCTGACCTA CGGCGTGCAG TGCTTCAGCC GCTACCCCG
300    ACCACATGAA GCAGCACGAC TTCTTCAAGT CCGCCATGCC CGAAGGCTAC GTCCAGGAG
360    CGCACCATCT TCTTCAAGGA CGACGGCAAC TACAAGACCC GCGCCGAGGT GAAGTTCGA
420    GGGCGACACC CTGGTGAACC GCATCGAGCT GAAGGGCATC GACTTCAAGG AGGACGGCA
480    ACATCCTGGG GCACAAGCTG GAGTACAACT ACAACAGCCA CAACGTCTAT ATCATGGCC
540    GACAAGCAGA AGAACGGCAT CAAGGTGAAC TTCAAGATCC GCCACAACAT CGAGGACGG
600    CAGCGTGCAG CTCGCCGACC ACTACCAGCA GAACACCCCC ATCGGCGACG GCCCCGTGC
660    TGCTGCCCGA CAACCACTAC CTGAGCACCC AGTCCGCCCT GAGCAAAGAC CCCAACGAG
720    AAGCGCGATC ACATGGTCCT GCTGGAGTTC GTGACCGCCG CCGGGATCAC TCTCGGCAT
780    GGACGAGCTG TACAAGTAA (SEQ ID NO:1)
```

Figure 2.

```
  1    MGRGSHHHHH HKLPKKKRKV LEMVSKG*EL FTGVVPILVE LDGDVNGHKF
 51    SVSGEGEGDA TYGKLTLKFI CTTGKLPVPW PTLVTTLTYG VQCFSRYPDH
101    MKQHDFFKSA MPEGYVQERT IFFKDDGNYK TRAEVKFEGD TLVNRIELKG
151    IDFKEDGNIL GHKLEYNYNS HNVYIMADKQ KNGIKVNFKI RHNIEDGSVQ
201    LADHYQQNTP IGDGPVLLPD NHYLSTQSAL SKDPNEKRDH MVLLEFVTAA
251    GITLGMDELY K (SEQ ID NO:2)
```

Figure 5

```
  1    ATGGGAAGAG GATCGCATCA CCACCATCAT CATAAGCTTC CAAAGAAGAA 51
       GAGGAAGGTT CTCGAGATGG TTTCTAAGGG TGAGGAACTT TTCACTGGTG
101    TGGTTCCAAT TCTCGTTGAG CTTGATGGTG ATGTTAACGG ACACAAGTTC
151    TCTGTTTCTG GTGAAGGTGA AGGTGATGCT ACTTAAGGAA AGCTTACTCT
201    CAAGTTCATC TGCACTACTG GAAAGCTTCC AGTTCCATGG CCAACTCTTG
251    TTACTACTTT CGGATACGGT GTTCAATGCT TCGCTAGGTA TCCAGATCAT
301    ATGAGGCAGC ACGATTTCTT CAAGTCTGCT ATGCCAGAGG GATATGTTCA
351    AGAGAGGACT ATCTTCTTCA AGGATGATGG CAACTACAAG ACTAGGGCTG
401    AGGTTAAGTT CGAGGGTGAT ACTCTTGTGA ACAGGATTGA GCTTAAGGGC
451    ATCGATTTCA AAGAGGATGG AAACATTCTC GGCCACAAGC TTGAGTACAA
501    CTACAATTCT CACAACGTGT ACATCATGGC TGATAAGCAG AAGAACGGCA
551    TCAAGGTTAA CTTCAAGATC AGGCACAACA TCGAGGATGG ATCTGTTCAA
601    CTTGCTGATC ATTACCAGCA GAACACTCCA ATTGGAGATG GACCAGTTCT
651    TCTTCCTGAT AACCACTACC TTTCTTACCA GTCTGCTCTT TCCAAGGATC
701    CAAATGAGAA GAGGGATCAC ATGGTGCTTT GGAGTTTGT TACTGCTGCT
751    GGAATCACTC TTGGCATGGA TGAACTCTAC AAGTGA
```

Figure 6.

```
  1    MGRGSHHHHH HKLPKKKRKV YLEMVSKGEE LFTGVVPILV ELDGDVNGHK
 51    FSVSGEGEGD AT*GKLTLKF ICTTGKLPVP WPTLVTTFGY GVQCFARYPD
101    HMRQHDFFKS AMPEGYVQER TIFFKDDGNY KTRAEVKFEG DTLVNRIELK
151    GIDFKEDGNI LGHKLEYNYN SHNVYIMADK QKNGIKVNFK IRHNIEDGSV
201    QLADHYQQNT PIGDGPVLLP DNHYLSYQSA LSKDPNEKRD HMVLLEFVTA
251    AGITLGMDEL YK
```

TARGETED ALTERATION OF DNA WITH OLIGONUCLEOTIDES

CROSS REFERENCE TO RELATED APPLICATIONS

This application is a national stage filing under 35 U.S.C. §371 of International Application No. PCT/NL2011/050805, filed on Nov. 25, 2011, and claims the benefit of priority of U.S. Provisional Application No. 61/419,183, filed on Dec. 2, 2010, and of Dutch Application No. 2005809, filed on Dec. 3, 2010. All of these applications are incorporated herein by reference in their entirety.

TECHNICAL FIELD

The current invention relates to a method for targeted alteration of acceptor DNA, for example duplex acceptor DNA. The method comprises use of at least two oligonucleotides, each oligonucleotide having at least one mismatch relative to the targeted (duplex) acceptor DNA. The mismatch of the first oligonucleotide is directed to a nucleotide in the first strand of the duplex and the mismatch of the second oligonucleotide is directed to the nucleotide in the second strand that forms a base-pair with the nucleotide in the first strand. These mismatches are located at specific positions within said oligonucleotides. Also provided is a kit that comprises instructions for performing the method according to the inventions, and in a preferred embodiment, comprises oligonucleotides suitable for use in the method.

BACKGROUND OF THE INVENTION

Genetic modification is the process of deliberately creating changes in the genetic material of living cells. Often the purpose is to modify a genetically encoded biological property of that cell, or of the organism of which the cell forms part or into which it can regenerate. These changes can take the form of deletion of parts of the genetic material, addition of exogenous genetic material, or changes in the existing nucleotide sequence of the genetic material, for example by substituting one nucleotide for another.

Methods for the genetic modification of eukaryotic organisms have been known for over 20 years, and have found widespread application in plant, human and animal cells and microorganisms for improvements in the fields of agriculture, human health, food quality and environmental protection.

A common genetic modification methodology consists of adding exogenous DNA fragments to the genome of a cell, which may then confer a new property to that cell or organism over and above the properties encoded by already existing genes (including applications in which the expression of existing genes will thereby be suppressed).

Although these methods may have some effectiveness in providing the desired properties to a target, these methods are nevertheless not very precise. There is, for example, no control over the genomic positions in which the exogenous DNA fragments are inserted (and hence over the ultimate levels of expression). In addition, the desired effect will have to manifest itself over the natural properties encoded by the original and well-balanced genome. On the contrary, methods of genetic modification that will result in the addition, deletion or conversion of nucleotides in predefined genomic loci will allow the precise and controllable modification of existing genes.//esp Oligonucleotide-directed Targeted Nucleotide Exchange (TNE) is a method that is based on the delivery into the eukaryotic cell of (synthetic) oligonucleotides (molecules consisting of short stretches of nucleotides and/or nucleotide-like moieties that resemble DNA in their Watson-Crick base pairing properties, but may be chemically different from DNA; (Alexeev and Yoon, 1998); (Rice et al., 2001); (Kmiec, 2003)).

By deliberately designing a mismatch nucleotide in the homology sequence of the oligonucleotide, the mismatch nucleotide may induce changes in the genomic DNA sequence to which the nucleotide may hybridize. This method allows the conversion of one or more nucleotides in the target, and may, for example, be applied to create stop codons in existing genes, resulting in a disruption of their function, or to create codon changes, resulting in genes encoding proteins with altered amino acid composition (protein engineering).

Targeted nucleotide exchange (TNE) has been described in many organisms including plant, animal and yeast cells and is also referred to as Oligonucleotide-directed Mutagenesis (ODM).

The first examples of TNE using chimeric DNA:RNA oligonucleotides came from animal cells (reviewed in (Igoucheva et al., 2001)). TNE using chimeric DNA:RNA oligonucleotides has also been demonstrated in plant cells (Beetham et al., 1999; Kochevenko and Willmitzer, 2003; Okuzaki and Toriyama, 2004; Zhu et al., 2000; Zhu et al., 1999). In general, the frequencies reported in both plant and animal studies were too low for practical application of TNE on non-selectable chromosomal loci. TNE using chimeric oligonucleotides was also found to be difficult to reproduce (Ruiter et al., 2003), resulting in a search for alternative oligonucleotide designs giving more reliable results.

Several laboratories have focused on the use of single stranded (ss) oligonucleotides for TNE. These have been found to give more reproducible results in both plant and animal cells (Liu et al., 2002) (Parekh-Olmedo et al., 2005) (Dong et al., 2006). However, the greatest problem facing the application of TNE in cells of, in particular, higher organisms such as plants remains the relative low efficiency that has been reported so far. In maize a conversion frequency of $1 \times 10^{-4}$ has been reported (Zhu et al., 2000). Subsequent studies in tobacco (Kochevenko and Willmitzer, 2003) and rice (Okuzaki and Toriyama, 2004) have reported frequencies of $1 \times 10^{-6}$ and $1 \times 10^{-4}$ respectively.

TNE using various types of oligonucleotides has been the subject of various patent and patent applications including U.S. Pat. No. 6,936,467, U.S. Pat. No. 7,226,785, US579597, U.S. Pat. No. 6,136,601, US2003/0163849, US2003/0236208, WO03/013226, U.S. Pat. No. 5,594,121 and WO01/92512.

In U.S. Pat. No. 6,936,467 it is contemplated that the low efficiency of gene alteration obtained using unmodified DNA oligonucleotides is the result of degradation of the donor oligonucleotides by nucleases present in the reaction mixture or the target cell. It is proposed to incorporate modified nucleotides that render the resulting oligonucleotides (more) resistant against nucleases. These modifications are disclosed to preferably be located at the ends of the oligonucleotide whereas the mismatch is present at least 8 nucleotides from each terminal end.

U.S. Pat. No. 7,226,785 also discloses methods for targeted chromosomal genomic alterations using modified single-stranded oligonucleotides with at least one modified nuclease-resistant terminal region. TNE using modified single stranded oligonucleotides is also the subject of WO02/26967.

Because of the low efficiency of the current methods of TNE there remains a need for alternative and/or better TNE techniques. These can be used alone or in combination with existing TNE techniques, like those disclosed above and in the art, to improve efficiency. Accordingly, the present inventors have set out to improve on the existing TNE technology.

SUMMARY OF THE INVENTION

Technical Problem

The technical problem identified in the art is that the current available methodology for introducing specific and desired genetic changes in cells, for example for introducing specific genetic changes in the genome present in a plant cell, are hindered by low efficiency, making the techniques laborious and costly. There is a need to come to alternative and better TNE techniques.

One of the problems to be solved is therefore to provide for an alternative and/or better and/or additional method for the introduction of genetic change(s) in the genetic information, in particular duplex DNA sequences, as is present in cells. Preferably such method has improved efficiency in comparison to those described in the art. Such method would allow for the provision of cells with altered genetic information, more in particular for cells wherein a functionality of the cell has been changed by the introduction of the alteration in the target DNA. Such functionality may for example relate to altered properties of the protein encoded by a DNA sequence encompassing the DNA that has been altered by the method according to the invention.

The Solution to the Problem

The solution to the problem is presented in the accompanying claims.

Duplex or double-stranded DNA is a term very well known to the skilled person and refers to the two strands of DNA held in a double helix by complementary base pairing (Watson-Crick base-pairing) between A's and T's and between G's and C's.

The inventors have now found a new method for targeted alteration of a duplex DNA sequence comprising a first DNA sequence (comprised in the first strand) and a second DNA sequence (comprised in the second strand) which is the complement of the first DNA sequence.

The method takes advantage of at least two different and specifically designed donor oligonucleotides. Each of the two donor oligonucleotides comprises a domain that is capable of hybridizing to the target (under conditions that allow hybridization, as they are known to the skilled person). Each of the two donor nucleotides further comprises at least one mismatch in comparison to the targeted duplex DNA sequence, which mismatch is to be introduced in the targeted duplex DNA sequence.

The first oligonucleotide comprises a domain that is capable of hybridizing to said first DNA sequence (in the first strand) and the second oligonucleotide comprises a domain that is capable of hybridizing to said second DNA sequence (in the second strand).

The at least one mismatch in the first oligonucleotide is directed/relative to a nucleotide in the first DNA sequence and the at least one mismatch in the second oligonucleotide is directed/relative to the nucleotide in the second DNA sequence that forms a base-pair with the nucleotide in the first DNA sequence in the duplex DNA.

In the art it is advocated and common knowledge that a mismatch in a oligonucleotide should be present within the oligonucleotide, in other words "somewhere in the middle" of the oligonucleotide (see for example the various patent application discussed above, in particular U.S. Pat. No. 6,936,467 and U.S. Pat. No. 7,226,785).

Such oligonucleotide-design from the art, with a mismatch somewhere in the middle and flanked by various nucleotides at both sides, would prevent any skilled person from utilizing a set of at least two oligonucleotides as described above as these oligonucleotides will at least partially share complementary domains that may for example hybridize with each other therewith preventing use in targeted nucleotide exchange.

However, it has, surprisingly and unexpectedly, been found that the method according to the invention, using the at least two oligonucleotides described in detail herein, can be performed with good efficiency when the mismatch in each of the oligonucleotide is not located somewhere in the middle of the oligonucleotide but at specific locations. In particular it has been found that for efficient TNE the mismatch in the at least two oligonucleotides described herein should (for each oligonucleotide independently) be located at most two, preferably at most one nucleotide from the 3' end of an oligonucleotide. Most preferably the at least one mismatch is at the 3' end of the (ss) oligonucleotide.

In contrast to the general belief that any mismatch should be in a central part of a oligonucleotide, and that, for example, modifications at the 5' end and the 3' end of the oligonucleotide should be introduced to prevent premature degradation of the oligonucleotide by nucleases (see e.g. U.S. Pat. No. 6,936,467), it was now found that having a mismatch in the oligonucleotide zero, one or at most two nucleotide(s) from the 3' end provides for oligonucleotides that can advantageously be used in methods of targeted nucleotide exchange, i.e. in methods for targeted alteration of a duplex DNA sequence as described herein.

With the above it has now become possible to target at the same time a nucleotide in the first DNA sequence and the nucleotide in the second DNA sequence that forms a base-pair with the nucleotide in the first DNA sequence in the duplex DNA by using the at least two oligonucleotides as described herein, further unexpectedly improving targeted nucleotide exchange.

Each of the oligonucleotides comprising the at least one mismatch zero, one or at most two nucleotide(s) from the 3' end and as described herein may be further modified by the inclusion of modified nucleotides, i.e. nucleotides having a base modification, a backbone modification, a sugar modification and/or a modification at the 3' end and/or 5' end of said nucleotide. These modifications include well-known modifications to either improve binding/hybridization of the oligonucleotides to the target sequence and/or to prevent or inhibit breakdown of the oligonucleotides by so-called nucleases. Examples of such modified nucleotides include locked nucleic acids, or nucleotides having phosphorothioate linkages. However, as shown in example 2, it is not required that the first or the second oligonucleotide according to the invention incorporates nucleotides having phosphorothioate linkages nor is it required that any other type of modified nucleotide is incorporated.

BRIEF DESCRIPTION OF THE DRAWINGS

FIG. 1 Nucleotide sequence of the GFP ORF containing a stop codon (SEQ ID NO:1).

FIG. 2 Amino acid sequence of the GFP-STOP protein. The position of the stop codon is represented by the asterisk (SEQ ID NO:2).

FIG. 5 shows the nucleotide sequence of the YFP-STOP construct (SEQ ID NO:12). The nucleotide at position 186 has been altered (C to A), resulting in an in-frame stop codon.

FIG. 6 shows the protein sequence of the YFP-STOP (SEQ ID NO:13). The position of the stop codon in the protein is indicated by an asterisk.

DEFINITIONS

Figure 3:
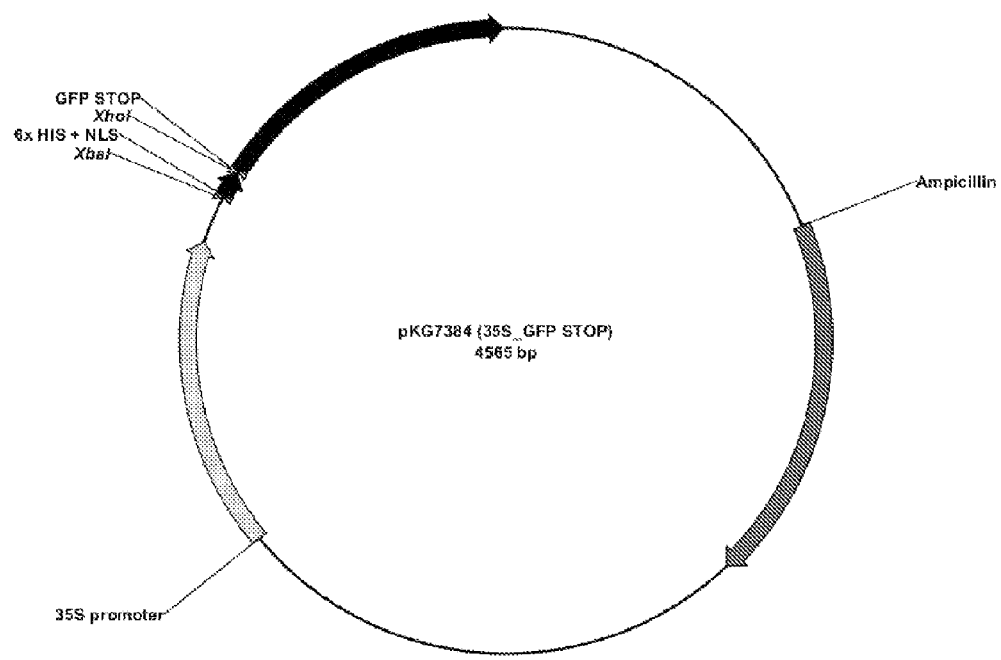
FIG. 3 The constructs used in this study.
Figure 3:
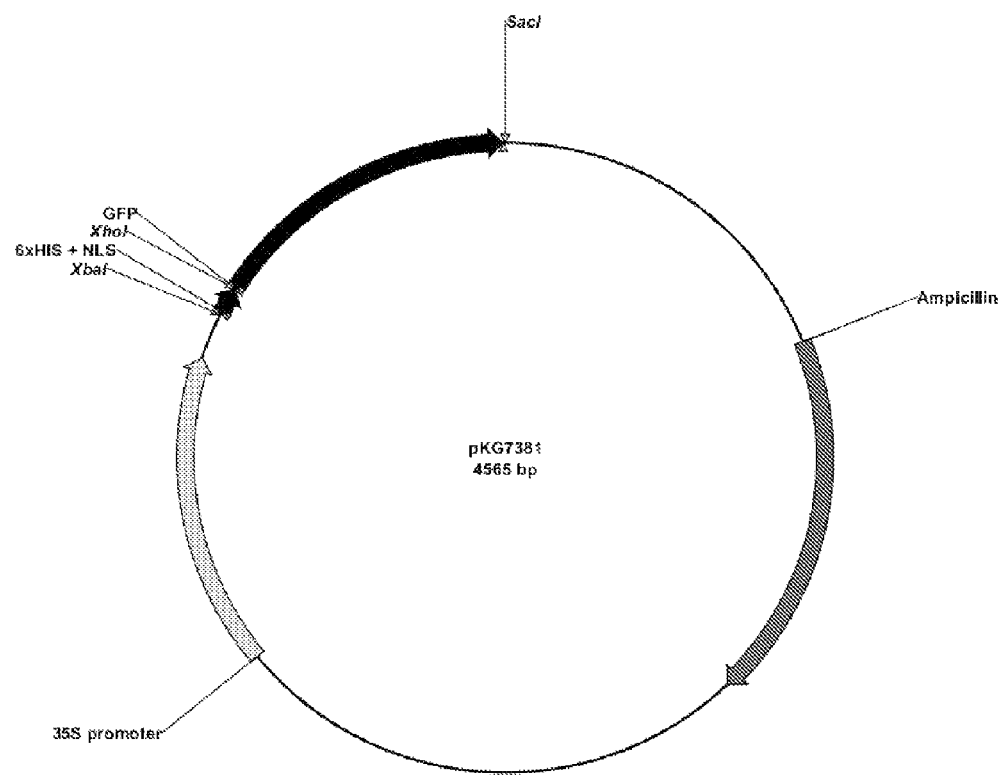

In the following description and examples, a number of terms are used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

As used herein, the singular forms "a," "an" and "the" include plural referents unless the context clearly dictates otherwise. For example, a method for isolating "a" DNA molecule, as used above, includes isolating a plurality of molecules (e.g. 10's, 100's, 1000's, 10's of thousands, 100's of thousands, millions, or more molecules). In particular, the invention described herein takes advantage of the use of at least two oligonucleotides. Where in the description reference is made to "a" or "the" oligonucleotide, this is not to be understood by the skilled person to indicate the absence of one of the at least two oligonucleotides, but is to be understood to indicate that reference is made, independently, to one, two, or more or all of the at least two oligonucleotides applied in the method according to the invention, unless the context clearly dictates otherwise. For example, if it is mentioned that the oligonucleotide may comprise an LNA-nucleotide, this is to be understood by the skilled person that one of the oligonucleotides may comprise such LNA-residue, but also that both of the at least two oligonucleotides may comprise such LNA-residue.

In this document and in its claims, the verb "to comprise" and its conjugations is used in its non-limiting sense to mean that items following the word are included, but items not specifically mentioned are not excluded.

Methods of carrying out the conventional techniques used in method of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N.Y., 1989; Ausubel et al., Current Protocols in Molecular Biology, John Wiley & Sons, New York, 1987 and periodic updates; and the series Methods in Enzymology, Academic Press, San Diego.

A nucleic acid according to the present invention may include any polymer or oligomer of pyrimidine and purine bases, preferably cytosine, thymine, and uracil, and adenine and guanine, respectively (See Albert L. Lehninger, *Principles of Biochemistry*, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

(Synthetic) oligonucleotide: single-stranded DNA molecules having preferably from about 5 to about 150 bases, which can be synthesized chemically are referred to as synthetic oligonucleotides. In general, these synthetic DNA molecules are designed to have a unique or desired nucleotide sequence, although it is possible to synthesize families of molecules having related sequences and which have different nucleotide compositions at specific positions within the nucleotide sequence. The term synthetic oligonucleotide will be used to refer to DNA molecules having a designed or desired nucleotide sequence.

"Targeted Nucleotide Exchange" or "TNE". Targeted nucleotide exchange (TNE) is a process by which at least one synthetic oligonucleotide, at least partially complementary to a site in a chromosomal or an episomal gene directs the reversal of a nucleotide at a specific site. TNE has been described using a wide variety of oligonucleotides and targets. Some of the reported oligonucleotides are RNA/DNA chimeras, contain terminal modifications to impart nuclease resistance.

DETAILED DESCRIPTION OF THE INVENTION

In one aspect, the invention pertains to a method for targeted alteration of a duplex acceptor DNA sequence comprising a first DNA sequence and a second DNA sequence which is the complement of the first DNA sequence.

The method comprises combining a/the duplex acceptor DNA sequence with at least two donor oligonucleotides, being a first oligonucleotide and a second oligonucleotide. The first oligonucleotide comprises at least one domain that is capable of hybridizing to the first DNA sequence and further comprises at least one mismatch with respect to the first DNA sequence. This at least one mismatch is positioned at most 2 nucleotides from the 3' end of said first oligonucleotide. Preferably the mismatch is positioned at most 1 nucleotide from the 3' end of said oligonucleotide, even more preferably the mismatch is 0 nucleotides from the 3' end of said oligonucleotide, in other words, is at the 3' end of said oligonucleotide. The second oligonucleotide comprises at least one domain that is capable of hybridizing to the second DNA sequence and further comprises at least one mismatch with respect to the second DNA sequence. This at least one mismatch is positioned at most 2 nucleotides from the 3' end of said second oligonucleotide. Preferably the mismatch is positioned at most 1 nucleotide from the 3' end of said oligonucleotide, even more preferably the mismatch is 0 nucleotides from the 3' end of said oligonucleotide, in other words, is at the 3' end of said oligonucleotide. The at least one mismatch in the first oligonucleotide is relative to a nucleotide in the first DNA sequence of the duplex acceptor DNA sequence and the at least one mismatch in the second oligonucleotide is relative to a nucleotide in the second DNA sequence of the duplex acceptor DNA, wherein said nucleotides occupy complementary positions in the duplex acceptor DNA (i.e. can form a base pair in the duplex acceptor DNA).

In other words, the at least two oligonucleotides target the same base pair in the duplex acceptor DNA, the mismatch of the first oligonucleotide targets the nucleotide in the first DNA sequence and the mismatch of the second oligonucleotide targets the complementary nucleotide in the second DNA sequence in the duplex DNA.

In other words, there is provided a method for targeted alteration of a duplex acceptor DNA sequence comprising a first DNA sequence and a second DNA sequence which is the complement of the first DNA sequence, the method comprising combining the duplex acceptor DNA with at least two oligonucleotides wherein the first oligonucleotide comprises a domain that is capable of hybridizing to the first DNA sequence and further comprises a mismatch relative to a nucleotide in the first DNA sequence and the second oligonucleotide comprises a domain that is capable of hybridizing to the second DNA sequence and further comprises a mismatch relative to a nucleotide in the second DNA sequence and wherein said nucleotides in the first DNA sequence and the second DNA sequence occupy complementary positions in the duplex acceptor DNA (e.g. form a base pair in the duplex acceptor DNA), and wherein, independently, the mismatch in the first oligonucleotide and the mismatch in the second oligonucleotide is positioned at most 2 nucleotides from the 3' end of said oligonucleotide.

As mentioned above, each oligonucleotide of the at least two oligonucleotides according to the invention comprises a domain that is capable of hybridizing either to the first or the second DNA sequence (under conditions that allow hybridization, as known to the skilled person). Preferably, the domain that is capable of hybridizing to the first DNA sequence comprises at least one mismatch with respect to the first DNA sequence, or the mismatch is positioned directly adjacent to said domain (as long as the mismatch is at most 2 nucleotides from the 3' end of said oligonucleotide). Preferably, the domain that is capable of hybridizing to the second DNA sequence comprises at least one mismatch with respect to the second DNA sequence, or the mismatch is positioned directly adjacent to said domain (as long as the mismatch is at most 2 nucleotides from the 3' end of said oligonucleotide).

The method according to the invention allows for the specific and selective alteration of one or more nucleotides at (a) specific site(s) of an acceptor DNA sequence by means of oligonucleotides directed to both strands of the duplex DNA and each directed to a different nucleotide of the same base-pair as in present in the duplex DNA.

In particular the targeted alteration can be performed within a target cell containing the duplex acceptor DNA sequence by the introduction into that cell of the at least two oligonucleotides according to the invention, i.e. a first oligonucleotide having, in comparison to the first DNA sequence to which it may hybridize, at least one mismatch and wherein said at least one mismatch is positioned at most 2, preferably at most 1 nucleotide from the 3' end of said oligonucleotide and a second oligonucleotide having, in comparison to the second DNA sequence to which it may hybridize, at least one mismatch and wherein said at least one mismatch is positioned at most 2, preferably at most 1 nucleotide from the 3' end of said oligonucleotide, and wherein the mismatch in the first oligonucleotide and the mismatch in the second oligonucleotide are each directed to a different nucleotide of the same base-pair in the duplex DNA.

Most preferably said at least one mismatch is at the 3' end of the oligonucleotide, even more preferably said at least one mismatch is at the 3' end in both oligonucleotides. The result of the method is the targeted alteration in a strand of one or more nucleotides so that the sequence of the target DNA sequence is altered. The invention may preferably be performed in vivo but may also be performed ex vivo or in vitro.

Within the context of the current invention, the duplex DNA sequence comprises a first DNA sequence and a second DNA sequence. The second DNA sequence is the complement of the first DNA sequence and pairs to it to form the duplex. For example, a complement of a first DNA sequence ATTT (in the 5' to 3' direction) is TAAA (in the 3' to 5' direction). This second DNA sequence pairs with the first DNA sequence to form a duplex. In case the duplex DNA sequence is, for example, part of a gene, the first DNA sequence may be either on the sense strand or anti-sense strand.

The DNA of the duplex DNA sequence may be any type of DNA, such as genomic DNA, DNA derived from genomic DNA, linear DNA, artificial chromosomes, nuclear chromosomal DNA, organellar DNA, BACs, YACs, plasmid DNA, or episomal DNA. The DNA sequence may be part of an intron or an exon, coding or non-coding, regulating expression or not.

The oligonucleotides used in the method disclosed herein are preferably single stranded and comprise at least one domain that is capable of hybridizing to either the first DNA sequence (the first oligonucleotide) or the second DNA sequence (the second oligonucleotide).

For each of the two oligonucleotide, and independently from each other, the at least one mismatch with respect to the DNA sequence to be altered and which mismatch is positioned 0, 1 or 2 nucleotides from the 3' end of the oligonucleotide, is either comprised in the domain that is capable of hybridizing to the first (for the first oligonucleotide) or second (for the second oligonucleotide) DNA sequence or is directly adjacent to the domain.

The at least one domain in the oligonucleotide may thus comprise at least one mismatch with respect to the DNA sequence to be altered or is directly next/adjacent to the mismatch. In other words, the oligonucleotide comprises a domain consisting of adjacent nucleotides than can hybridize, under the conditions of the experiment, with the first or second DNA sequence of the duplex acceptor DNA sequence, and either comprises a mismatch with respect to said first or second DNA sequence or the mismatch is positioned directly next to said domain (and wherein the mismatch is positioned 0, 1 or 2 nucleotides from the 3' end of the oligonucleotide).

For example, if the domain is (in the 5' to 3' direction) positioned up to 3 nucleotides from the 3' end, the mismatch may be directly next to the domain 2 nucleotides from the 3' end of the oligonucleotide. For example if the domain is (in the 5' to 3' direction) positioned up to 1 nucleotide from the 3' end, the mismatch can be comprised in the domain, e.g. localized 2 nucleotides from the 3' end, of be directly adjacent to the domain, i.e. localized 0 nucleotides from the 3' end, in other words at the 3' end of the oligonucleotide.

It is to be understood that choices with respect to the position of the mismatch in each of the at least two oligonucleotides can be made independently from the other oligonucleotide. In other words, in case the mismatch in the first oligonucleotide is, for example, at the 3' end of said oligonucleotide, the mismatch in the second oligonucleotide not necessarily has to be positioned at the 3' end of said oligonucleotide, but may also be positioned, for example at most 2 nucleotides from the 3' end of said oligonucleotide.

It is to be understood by the skilled person that within the context of the current invention, and where reference is made to the mismatch or the mismatch comprised in the domain that is capable of hybridizing with the first or second DNA sequence, these include any mismatch comprised in the domain or positioned directly adjacent to the domain, as long as the mismatch is positioned 2, 1 or 0 nucleotides from the 3' end of the oligonucleotide.

In preferred embodiments the first oligonucleotide comprises preferably no more than one mismatch with respect to the first DNA sequence, and/or the second oligonucleotide comprises preferably no more than one mismatch with respect to the second DNA sequence (both directed to a different nucleotide of a base-pair as present in the duplex DNA).

In certain embodiments, more than one mutation can be introduced into the target DNA, either simultaneously or successively. The oligonucleotide can accommodate more than one mismatch on either adjacent or on removed locations on the oligonucleotide. In certain embodiments the oligonucleotide can comprise two, three, four or more mismatch nucleotides which may be remote (i.e. non-adjacent). The oligonucleotide can comprise further domains to accommodate this. The mismatches may be in the same or in different domains.

It will be understood by the skilled person that the oligonucleotides according to the invention may further comprise non-hybridizing parts, in other words adjacent nucleotides that do not hybridize with the first or second DNA sequence, for example as these parts are not complementary to any sequence in the first or second DNA sequence.

In a preferred embodiment the first oligonucleotide comprises one domain that is capable of hybridizing to the first DNA sequence and comprises, or is directly adjacent to at least one mismatch, preferable one mismatch, with respect to the DNA sequence to be altered and the second oligonucleotide comprises one domain that is capable of hybridizing to the second DNA sequence and comprises, or is directly adjacent to at least one mismatch, preferable one mismatch, with respect to the DNA sequence to be altered, wherein the at least one mismatch in the first oligonucleotide is relative to a nucleotide in the first DNA sequence of the duplex acceptor DNA sequence and wherein the at least one mismatch in the second oligonucleotide is relative to a nucleotide in the second DNA sequence of the duplex acceptor DNA, and wherein said nucleotides occupy complementary positions in the duplex acceptor DNA (e.g. form a base pair in the duplex acceptor DNA).

In such embodiment the oligonucleotide may, in principal, comprise more than one domain that is capable of hybridizing to the respective first or second DNA sequence, however only one of the domains may comprise, or be directly adjacent to, the at least one mismatch (or the one mismatch), as disclosed herein. In another preferred embodiment the oligonucleotide, preferably both oligonucleotides, comprise(s) only one domain that can hybridize to the duplex DNA. Such domain is located near or at the 3' end of the oligonucleotide and includes the mismatch, or is directly adjacent to the mismatch.

The oligonucleotides that are used as donors in the method disclosed herein can vary in length but generally vary in length between 10 and 500 nucleotides, with a preference for 11 to 100 nucleotides, preferably from 15 to 90, more preferably from 20 to 70.

The domain may consist of at least 5 nucleotides, including the mismatch, but may also consist of all nucleotides, including the mismatch, of the oligonucleotide. In case the mismatch is directly adjacent to the domain, the domain may consist of at least 5 nucleotides, but may also consist of all nucleotides of the oligonucleotide, except for the mismatch. Domain(s) in the oligonucleotide are typically in the order of at least 5, 10, preferably 15, 20, 25 or 30 nucleotides.

The oligonucleotides according to the invention comprise at least one mismatch that is positioned at most 2, preferably at most 1 nucleotide from the 3' end of said oligonucleotide. Preferably said (at least one) mismatch is at the 3' end of the oligonucleotide, most preferably said (at least one) mismatch is at the 3' end of the oligonucleotide in both the first oligonucleotide and the second oligonucleotide. A person skilled in the art understands what the term 3' end encompasses. A single-stranded non-circular DNA molecule has two ends, the 3' end and the 5' end (also referred to as "three prime end" and "five prime end").

The 5' end of a single strand nucleic acid designates that specific nucleotide of which the C-5 carbon atom forms the terminal carbon atom of the sugar-phosphate backbone. The C-5 carbon atom may or may not be linked to a phosphate group by a phosphodiester bond, but this phosphate group in turn does not form any linkage with another nucleotide.

The 3' end of a single strand nucleic acid designates that specific nucleotide of which the C-3 carbon atom, is not linked to any other nucleotides, whether by means of a phosphate diester bond or otherwise. The C-5 atom is the $5^{th}$ carbon atom of the ribose or deoxyribose molecule and does not form part of the furanose ring, starting counting from the C atom directly adjacent to both the oxygen of the furanose ring and the nucleobase. The C-3 atom is the $3^{rd}$ carbon atom of the ribose or deoxyribose molecule and forms part of the furanose ring, starting counting from 1 which is the C atom directly adjacent to both the oxygen of the furanose ring and the nucleobase.

The term "mismatch positioned 2 nucleotides from the 3' end" indicates that the mismatch is two nucleotides from the nucleotide at the 3' terminus of the oligonucleotide. The term "mismatch positioned 1 nucleotide from the 3' end" indicates that the mismatch is one nucleotide from the nucleotide at the 3' terminus of the oligonucleotide. The term "mismatch positioned 0 nucleotides from the 3' end" indicates that the mismatch is the nucleotide at the 3' terminus of the oligonucleotide.

In a preferred embodiment of the method described herein, the mismatch in the first oligonucleotide or the mismatch in the second oligonucleotide is, independently, positioned at most 1 nucleotide from the 3' end of said oligonucleotide, more preferably said at least one mismatch is at the 3' end of the oligonucleotide, preferably the mismatch in both oligonucleotides is at the 3' end of the respective oligonucleotides.

Also preferred in the method described herein is that the domain in the first oligonucleotide and/or in the second oligonucleotide comprises or is directly adjacent to the at least one mismatch.

In addition, preferably in the method described herein, the first oligonucleotide is complementary to the first DNA sequence except for the mismatch and/or the second oligonucleotide is complementary to the second DNA sequence except for the mismatch. In such embodiment the first oligonucleotide thus comprises one mismatch with respect to the first DNA sequence and the second oligonucleotide comprises one mismatch with respect to the second DNA sequence (each direct to a different nucleotide of a base-pair in the duplex DNA). Such oligonucleotide is complementary to the first or second DNA sequence over the entire length of the oligonucleotide except for the one mismatch positioned at most 2, preferably at most 1 nucleotide from the 3' end of said oligonucleotide, most preferably said mismatch is at the 3' end of the oligonucleotide. In another embodiment, the oligonucleotide is (in the 5' to 3' direction) complementary to the first or second DNA sequence over the entire length of the oligonucleotide up to the position of the mismatch (localized 2, 1 or 0 nucleotides from the 3' end). Even more preferably, the mismatch in the first oligonucleotide is at the 3' end and the mismatch in the second oligonucleotide is at the 3' end, and the first oligonucleotide is complementary to the first DNA sequence over the entire length of the oligonucleotide, except for the mismatch, and the second oligonucleotide is complementary to the second DNA sequence over the entire length of the oligonucleotide, except for the mismatch.

In another preferred embodiment of the method described herein, the first oligonucleotide and/or the second oligonucleotide comprises at least one section that contains at least one modified nucleotide, wherein the modification is selected from the group consisting of a base modification, a 3' and/or 5' end base modification, a backbone modification or a sugar modification.

The base modification, 3' and/or 5' end base modifications, backbone modification, and/or sugar modifications can be incorporated into the oligonucleotides to increase the (binding/hybridization) affinity of the oligonucleotides to the target sequence and, either independently or additionally, to increase the oligonucleotides resistance against cellular nucleases. However, as shown in example 2, it is not required that the first or the second oligonucleotide incorporates any modified nucleotide.

Any modification of a nucleotide in an oligonucleotide that provides an oligonucleotide suitable for use in the method according to the invention (and comprising at least one mismatch positioned at most 2, preferably at most 1 nucleotide from the 3' end of said oligonucleotide, most preferably said mismatch is at the 3' end of the oligonucleotide) can advantageously be used. It will be understood by the skilled person that a modification is relative to any one of a naturally occurring A, C, T, G nucleotides.

Advantageously, although not essential to the invention, the first and/or the second oligonucleotide for use in the method according to the invention may comprise modified nucleotides. In case both the first and the second oligonucleotide comprise modification(s), the modifications of the first may be the same as or different from the modifications of the second. In particular, any of the modifications discussed below may be incorporated in the first and/or the second oligonucleotide according to the invention.

For example, the first and/or the second oligonucleotide may comprise modification(s) that increase the resistance of the oligonucleotide against cellular nucleases, if compared to naturally occurring A, T, C, and G nucleotides. These modifications may include base modifications, backbone modifications, and/or sugar modifications. Typically, such modified nucleotides that increase the resistance of the oligonucleotide against cellular nucleases may result in an increased stability of the oligonucleotide in a cellular environment, which may result in improved targeted nucleotide exchange. Preferably, the first and/or the second oligonucleotides for use according to the method of the invention comprises at least 1, preferably at least 2, more preferably at least 4, more preferably at least 6, most preferably at least 8 modified nucleotides that increase the resistance of the oligonucleotide against cellular nucleases if compared to naturally occurring A, T, C, and G nucleotides. Alternatively, or at the same time, the first and/or the second oligonucleotide for use according to the method of the invention comprises at most 25, preferably at most 20, more preferably at most 15, most preferably at most 10 modified nucleotides that increase the resistance of the oligonucleotide against cellular nucleases if compared to naturally occurring A, T, C, and G nucleotides. Such modified nucleotides may be positioned at any position within the first and/or the second oligonucleotide, preferably within 20 nucleotides, preferably within 15, more preferably within 10, even more preferably within 8, even more preferably within 6 nucleotides from the 3' end and/or 5' end of the respective oligonucleotide, and most preferably at the last nucleotides at the 3' end and/or at the last nucleotides at the 5' end. As the mismatch which is to be incorporated in the target DNA sequence is located zero, one, or at most two nucleotide(s) from the 3' end of the oligonucleotides, it is particularly preferred that such modified nucleotide(s) protect the 3' side against cellular nucleases and thus are positioned on the 3' end of the first and/or the second oligonucleotide, such as within 20, 15, 10, 9, 8, 7, 6, or 4 nucleotides from the 3' end. However, as described earlier, and as shown in example 2, it is not essential to the invention that the oligonucleotide indeed includes modified nucleotides that increase resistance of the oligonucleotide against cellular nucleases.

Various of such modified nucleotides are mentioned herein, which increase the resistance of the oligonucleotide against cellular nucleases if compared to naturally occurring A, T, C, and G nucleotides and which may be incorporated in the first and/or the second oligonucleotide for use in the method according to the invention. Such modified nucleotide may be a nucleotide having phosphorothioate linkage(s), but may also be a phosphoramidite, a methylphosphonate, or a nucleotide with nonphosphate internucleotide bonds such as carbonates, carbamates, siloxane, sulfonamides and polyamide nucleic acid. Also, the modified nucleotides conferring cellular nuclease resistance as described in WO0226967 may be used, such as LNA (Locked Nucleic Acid), or any other modified nucleotide that improves cellular nuclease resistance of the oligonucleotide as known by the skilled person.

Alternatively or additionally to the above-described nuclease resistance conferring modified nucleotides, the first and/or the second oligonucleotide for use in the method according to the invention may comprise modified nucleotides having a higher binding affinity to the target DNA sequence if compared to naturally occurring A, T, C, and G nucleotides. These modification may include base modifications, backbone modifications, and/or sugar modifications. Typically, such modified nucleotides having increased binding affinity will affect stronger base-pairing with the target sequence, which may result in an increased stability of the hybrid between the oligonucleotide and the target sequence, which is believed to result in improved targeted nucleotide exchange. Preferably, the first and/or the second oligonucleotide for use according to the method of the invention comprises at least 1-10, preferably 1-8, more preferably 1-6, even more preferably 1-4, such as 1, 2, 3, or 4, even more preferably 2 modified nucleotides having a higher binding affinity to the target DNA sequence if compared to naturally occurring A, T, C, and G nucleotides. Such modified nucleotides as mentioned above may be positioned at any position within the first and/or the second oligonucleotide, preferably at a position one nucleotide away from the mismatch, preferably at most 2, 3, 4, 5, 6, or 7 nucleotides away from the mismatch. Preferably, such modified nucleotide is located at the 5' side of the mismatch, but it may also be opted to position such modified nucleotide at the 3' side of the mismatch if the mismatch is not positioned at the last nucleotide at the 3' end of the first and/or the second oligonucleotide.

Various examples of such modified nucleotides having a higher binding affinity to the target DNA sequence if compared to naturally occurring A, T, C, and G nucleotides are mentioned herein which may be incorporated in the oligonucleotide for use in the method according to the invention, including 2-OMe substitution, LNA (Locked Nucleic Acid), ribonucleotide, superA, superT, or any other type of modified nucleotide that improves binding affinity of the oligonucleotide to the target DNA sequence if compared to naturally occurring A, T, C, and G nucleotides, as known by the skilled person.

Determining whether a modified nucleotide confers increased resistance against cellular nucleases if compared to naturally occurring A, T, G, C nucleotides may for example be done by comparing half-life times of a oligonucleotide having said modified nucleotide with a oligonucleotide not having said modified nucleotide, in the presence of cellular nucleases as e.g. present in tomato extract, tomato cells, or in E. coli. If the half-life time of the first mentioned is higher, said modified nucleotide confers increased resistance against cellular nucleases if compared to naturally occurring A, T, G, C nucleotides. Determining whether a modified nucleotide confers higher binding affinity to the target DNA sequence if compared to naturally occurring A, T, C, or G nucleotides may for example be done by comparing melting temperature (Tm) of the duplex formed between the oligonucleotide having said modified nucleotide and its target over that formed by the oligonucleotide not having said modified nucleotide and its target. If the melting temperature of the first mentioned is higher, said modified nucleotide confers higher binding affinity to the target DNA sequence if compared to naturally occurring A, T, G, C nucleotides.

A section according to the present invention is to be understood to be any part of the oligonucleotide with a length of at least one nucleotide. For example, a section may comprise 1-10, preferably 1-6, more preferably 1-4, more preferably 1-2 nucleotides, and may be positioned at the 3' side and/or the 5' side of the mismatch. The at least one section can be part of a domain according to the invention; in other words the section may be in a domain that can hybridize with the first or second DNA sequence. Alternatively, the section may overlap with a domain, either completely or partially. In case of complete overlap the section may have the same length of the domain, but may also have a length with exceeds the length of the domain. In the case of partial overlap, the domain and the section share at least one nucleotide.

Depending on the type of modification used in the oligonucleotide there may be a preference for the modified nucleotide to be part of a domain that can hybridize with the first or second DNA sequence, and which domain comprises or is directly adjacent to the at least one mismatch positioned at most 2, preferably at most 1 nucleotide from the 3' end of said oligonucleotide, most preferably said mismatch is at the 3' end of the oligonucleotide. This is in particular the case for modified nucleotides with a higher binding affinity compared to naturally occurring A, C, T or G nucleotides with its complementary nucleotide.

Base modifications include, but are not limited to such modifications as for example described in WO0226967, including modifications at the C-5 position of pyrimidines such as 2'-deoxyuridine, 5-fluoro-2'-deoxyuridine, 5-bromo-2'-deoxyuridine and 5-methyl-2'-deoxycytidine. Other base modifications include synthetic and natural nucleobases like 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine, 2-thiocytosine, 5-halouracil and cytosine, 5-propynyl uracil and cytosine, 6-azo uracil, cytosine and thymine, 5-uracil, 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

End (3' and/or 5') modifications may include 2'-O—methyl bases, 3' amine groups, phosphorothioate linkages, or any other modification that is nuclease resistant. The skilled person is well aware of these kinds of modifications. Providing resistance to nuclease is believed to further improve the targeted nucleotide exchange.

Various backbone modifications, such as those mentioned in WO0226967, including phosphorothioates, phosphoramidites and methylphosphonates, and those with nonphosphate internucleotide bonds, such as carbonates, carbamates, siloxane, sulfonamides and polyamide nucleic acid will increase the resistance to cellular nucleases. Such backbone modifications are therefore useful in the oligonucleotide used in the method according to the invention.

In addition, sugar modifications, including but not limited to 2'-O— methyl, 2'-fluoro or 2'-methoxyethoxy can increase the thermodynamic stability of a formed duplex, and at the same time provide improved nuclease resistance.

Other examples of suitable modifications are described in WO2007073149. Modification of the donor oligonucleotides can for example comprise phosphorothioate linkages, 2-OMe substitutions, the use of LNAs (Locked nucleic acids), ribonucleotide and other bases that modify and preferably enhance, the stability of the hybrid between the oligonucleotide and the acceptor stand either by improving affinity binding to the target DNA or by inhibition of nuclease activity, or both.

All these types of modifications are well know to the skilled person and are readily available from various commercial sources. It will be understood by the skilled person that modification can be introduced in the first oligonucleotide independently of the second oligonucleotide used in the method described herein. For example, the first oligonucleotide may comprise such modifications as described above, whereas the second oligonucleotide does not. Alternatively the first oligonucleotide may comprise more, less or different modification at the same or at different positions in the oligonucleotide in comparison to the second oligonucleotide.

In an embodiment there is provided for a method according to the invention wherein a modified nucleotide is incorporated in the oligonucleotide, or in both, and wherein the modified nucleotide has a higher binding affinity compared to naturally occurring A, C, T, or G nucleotides with its complementary nucleotide, and wherein the modified nucleotide binds stronger to a nucleotide in the opposite position in the first or second DNA sequence as compared to a naturally occurring nucleotide complementary to the nucleotide in the opposite position in the first or second DNA sequence and/or wherein the modified nucleotide is a nuclease resistant nucleotide.

Preferably the modification is a base modification, a 3' end and/or 5' end base modification, a backbone modification or a sugar modification. As discussed above, the donor oligonucleotides according to the invention may contain modifications to improve the hybridization characteristics such that the donor exhibits increased affinity for the target DNA strand, which may make intercalation of the donor easier and/or increases the thermodynamic stability of the formed duplex (in comparison to the same oligonucleotide not comprising such modification, and under the same experimental circumstances). The donor oligonucleotide can independently or in addition be modified to become more resistant against nucleases, which may stabilize the duplex structure.

In the prior art a wide variety of modified nucleotides having a higher binding affinity compared to naturally occurring A, C, T, or G nucleotides with its complementary nucleotide, and wherein the modified nucleotide binds stronger to a nucleotide in the opposite position in the first or second DNA sequence as compared to a naturally occurring nucleotide complementary to the nucleotide in the opposite position in the first or second DNA sequence and/or wherein the modified nucleotide is a nuclease resistant nucleotide have been described (see for Example WO 2007073154 and the various modifications discussed above).

In certain embodiments, a modification is at a position one nucleotide away from to the mismatch, preferably 2, 3, 4, 5, 6 or 7 nucleotides away from the mismatch. In certain embodiments, modification is located at a position downstream from the mismatch. In certain embodiments, modification is located at a position upstream from the mismatch.

The domain that contains or is directly adjacent to the mismatch and the sections containing the modified nucleotide(s) may be overlapping. Thus, in certain embodiments, the domain containing the mismatch or directly adjacent to the mismatch is located at a different position on the oligonucleotide than the section of which the modification is considered. In certain embodiments, the domain incorporates one or more sections. In certain embodiments, sections can incorporate the domain. In certain embodiments, the domain and the sections may be located at the same position on the oligonucleotide and have the same length i.e. the sections coincide in length and position. In certain embodiments, there can be more than one section within a domain.

For the present invention, this means that the part of the oligonucleotide that contains the mismatch which is to alter the DNA duplex can be located at a different or shifted position from the part of the oligonucleotide that is modified.

Again, it will be understood by the skilled person that modifications can be introduced in the first oligonucleotide independently of the second oligonucleotide used in the method described herein. For example, the first oligonucleotide may comprise such modifications as described above, whereas the second oligonucleotide does not. Alternatively the first oligonucleotide may comprise more, less or different modifications at the same or at different positions in the oligonucleotide in comparison to the second oligonucleotide.

In a preferred embodiment the modified nucleotide is selected from the group consisting of LNAs and/or nucleotides having phosphorothioate bonds/linkage.

In a preferred embodiment, the modified nucleotide is a Locked Nucleic Acid. Locked Nucleic Acid (LNA) is a DNA analogue with interesting properties for use in antisense gene therapy and is known to the skilled person.

LNAs are bicyclic and tricyclic nucleoside and nucleotide analogues and may be incorporated in oligonucleotides. The basic structural and functional characteristics of LNAs and related analogues are disclosed in various publications and patents, including WO99/14226, WO00/56748, WO00/66604, WO98/39352, U.S. Pat. No. 6,043,060, and U.S. Pat. No. 6,268,490, all of which are incorporated herein by reference in their entireties.

LNA nucleosides are available for all the common nucleobases (T, C, G, A, U; for example from Exiqon (www.exiqon.com)) and are able to form base pairs according to standard Watson-Crick base pairing rules. When incorporated into a DNA oligonucleotide, LNA makes the pairing with a complementary nucleotide strand more rapid and increases the stability of the resulting duplex. In other words, LNA combines the ability to discriminate between correct and incorrect targets (high specificity) with very high bio-stability (low turnover) and unprecedented affinity (very high binding strength to target). In fact, the affinity increase recorded with LNA leaves the affinities of all previously reported analogues in the low-to-modest range.

LNA is an RNA analogue, in which the ribose is structurally constrained by a methylene bridge between the 2'-oxygen and the 4'-carbon atoms. This bridge restricts the flexibility of the ribofuranose ring and locks the structure into a rigid bicyclic formation. This so-called N-type (or 3'-endo) conformation results in an increase in the Tm (melting temperature) of LNA containing duplexes, and consequently higher binding affinities and higher specificities. Importantly, the favorable characteristics of LNA do not come at the expense of other important properties as is often observed with nucleic acid analogues.

LNA can be mixed freely with all other chemistries that make up the DNA analogue universe. LNA bases can be incorporated into oligonucleotides as short all-LNA sequences or as longer LNA/DNA chimeras. LNAs can be placed in internal, 3' or 5'-positions. However, due to their rigid bicyclic conformations, LNA residues sometimes disturb the helical twist of nucleic acid strands. It is hence generally less preferred to design an oligonucleotide with two or more adjacent LNA residues. Preferably, the LNA residues are separated by at least one (modified) nucleotide that does not disturb the helical twist, such as a conventional nucleotide (A, C, T, or G).

The originally developed and preferred LNA monomer (the [beta]-D-oxy-LNA monomer) has been modified into new LNA monomers. The novel [alpha]-L-oxy-LNA has been suggested to show superior stability against 3' exonuclease activity, and is also more powerful and more versatile than [beta]-D-oxy-LNA in designing potent antisense oligonucleotides. Also xylo-LNAs, L-ribo LNAs and other LNA's can be used, as disclosed in WO9914226, WO00/56748, WO00/66604 and J. Org. Chem., 2010, 75 (7), pp 2341-2349. In the present invention, any LNA of the above types is effective in achieving the goals of the invention, i.e. improved efficiency of TNE, with a preference for [beta]-D-LNA analogues.

As mentioned above, preferably, an LNA is at least one nucleotide away from a mismatch in a (or both of the at least two oligonucleotides) oligonucleotide used in the method according to the invention. Although in the art on TNE, LNA modification has been listed amongst a list of possible oligonucleotide modifications as alternatives for the chimeric molecules used in TNE, it has been found that when single-stranded DNA oligonucleotides, as used in the method according to the invention, are modified to contain LNA, TNE efficiency increase significantly to the extent that has presently been found when the LNA is positioned at least one nucleotide away from the mismatch, even more preferably one nucleotide from the mismatch. The oligonucleotide preferably does not contain more than about 75% (rounded to the nearest whole number of nucleotides) LNAs.

In another preferred embodiment, the modified nucleotide comprises a nucleotide having a phosphorothioate linkage. Many of the nucleotide modifications commercially available have been developed for use in antisense applications for gene therapy. The simplest and most widely used nuclease-resistant chemistry available for antisense applications (the "first generation" antisense-oligonucleotide) is the phosphorothioate (PS) linkage. In these molecules, a sulfur atom replaces a non-bridging oxygen in the oligonucleotide phosphate backbone (see, for example, FIG. 2 of WO2007073154, resulting in resistance to endonuclease and exonuclease activity.

For gene therapy, a phosphorothioate/phosphodiester chimera generally has one to four PS-modified internucleoside linkages on both the 5'- and 3'-ends with a central core of unmodified DNA. The phosphorothioate bonds can be incorporated, however, at any desired location in the oligonucleotide.

Preferably the modified nucleotide is an LNA or, even more preferably a nucleotide having a phosphorothioate linkage, more preferably the modified oligonucleotide having at least one, for example, one, two, three or four, phosphorothioate(s). Preferably the oligonucleotide contains at least one phosphorothioate at or near (e.g. within 1, 2, 3, 4, 5, 6, 7 nucleotides from) the 5' end of the oligonucleotide according to the invention.

In an embodiment there is provided that the oligonucleotide used in the method according to the invention comprises at least two, three, four, or five modified nucleotides. Preferably the oligonucleotide comprises two, three four or five modified nucleotides. Preferably the modifications are selected from the group consisting of LNAs and/or phosphorothioate bonds.

In certain preferred embodiments of the invention, the nucleotide in the oligonucleotide at the position of the mismatch can be modified. Whether or not the mismatch can be modified will depend to a large extent on the exact mechanism of the targeted nucleotide exchange or of the cell's DNA repair mechanism using the difference in affinity between the donor and acceptor strands. In a preferred embodiment the nucleotide at the position of the mismatch is not a modified nucleotide.

In an embodiment there is provided for a method according to the invention wherein the modified nucleotide is at least one nucleotide from the at least one mismatch located at most 2, preferably at most 1 nucleotide from the 3' end of said oligonucleotide, most preferably said at least one mismatch is at the 3' end of the oligonucleotide.

As discussed previously, it has been found that when single-stranded DNA oligonucleotides, as used in the method according to the invention, are modified to contain modified nucleotides, for example LNA, TNE efficiency increases significantly to the extent that has presently been found when the modified nucleotide, preferably LNA, is positioned at least one nucleotide away from the mismatch, even more preferably one mismatch from the mismatch. In other words, in a preferred embodiment, a modified nucleotide, preferably a LNA, is separated from the mismatch by at least one other nucleotide, which at least one other nucleotide is not a LNA, preferably not a modified nucleotide. However, in case of for example a phosphorothioate linkage, such linkage by be directly adjacent to the mismatch nucleotide.

In an embodiment there is provided for a method wherein the alteration of the duplex acceptor DNA is within a cell preferably selected from the group consisting of a prokaryotic cell, a bacterial cell, a eukaryotic cell, a plant cell, an animal cell, a yeast cell, a fungal cell, a rodent cell, a human cell, a non-human cell, and/or a(n) (non-human) embryonic cell. The invention is, in its broadest form, generically applicable to all sorts of organisms such as humans, animals, plants, fish, reptiles, insects, fungi, bacteria and so on. The invention can thus be performed within a cell selected from the group consisting of a prokaryotic cell, a bacterial cell, a eukaryotic cell, a plant cell, an animal cell, a yeast cell, a fungal cell, a rodent cell, a human cell, a non-human cell, and/or an embryonic cell. In a preferred embodiment, the cell is a plant cell.

There is also provided for a method as described herein wherein the duplex acceptor DNA is obtained from a prokaryotic organism, bacteria, a eukaryotic organism, a plant, an animal, a yeast, a fungus, a rodent, or a human. In a preferred embodiment the duplex acceptor DNA is obtained from a plant (or is plant DNA present in a plant cell).

In an embodiment of the invention, the alteration of the duplex acceptor DNA sequence is a deletion, a substitution and/or an insertion of at least one nucleotide. Preferably the alteration of the duplex DNA sequence is a deletion, a substitution and/or an insertion of no more than 5 nucleotides, preferably no more than 4, 3, 2, 1 nucleotide(s), most preferably one nucleotide (or in other words, one base-pair is modified in the duplex DNA). More preferably the alteration of the duplex acceptor DNA sequence is a substitution of no more than 5 nucleotides, preferably no more than 4, 3, 2, 1 nucleotide(s), most preferably one nucleotide.

In another embodiment there is provided a method according to the invention, wherein the duplex acceptor DNA is from genomic DNA, linear DNA, artificial chromosomes, mammalian artificial chromosomes, bacterial artificial chromosomes, yeast artificial chromosomes, plant artificial chromosomes, nuclear chromosomal DNA, organellar DNA, and/or episomal DNA including plasmids.

Indeed the invention is applicable for the modification of any type of DNA, such as those disclosed above. The invention can be performed in vivo as well as ex vivo or in vitro, for example by subjecting the DNA to be modified with the donor oligonucleotide in the presence of proteins that are capable of targeted nucleotide exchange, for instance, and in particular, proteins that are functional in the mismatch repair mechanism of the cell.

The delivery of the oligonucleotide to a cell can be achieved via electroporation or other conventional techniques that are capable of delivering either to the nucleus or the cytoplasm. In vitro testing of the method of the present invention can be achieved using the Cell Free system as is described i.a. in WO01/87914, WO03/027265, WO99/58702, WO01/92512. The oligonucleotide may comprise methylated nucleotides, non-methylated nucleotides or both.

The invention is, in its broadest form, applicable for many purposes for altering a cell, correcting a mutation by restoration to wild type, inducing a mutation, inactivating an enzyme by disruption of coding region, modifying bioactivity of an enzyme by altering coding region, modifying a protein by disrupting the coding region.

The invention also relates to the use of oligonucleotides essentially as described hereinbefore, for altering a cell, correcting a mutation by restoration to wild type, inducing a mutation, inactivating an enzyme by disruption of coding region, modifying bioactivity of an enzyme by altering coding region, modifying a protein by disrupting the coding region, mismatch repair, targeted alteration of (plant) genetic material, including gene mutation, targeted gene repair and gene knockout. Preferably the method according to the invention is for targeted alteration of duplex acceptor DNA obtained from a plant, present in a plant, or to be presented to a plant.

The invention further relates to kits, preferably comprising at least one, preferably both of the oligonucleotides used in the method according to the invention, and as defined herein, optionally in combination with proteins that are capable of TNE.

In particular, the kit comprises instructions for targeted alteration of a duplex DNA in accordance with the method described and claimed herein. The instructions comprise essentially a description of the steps of the method according to the invention described herein.

In particular there is provided a kit comprising instructions for performing a method for targeted alteration of a duplex acceptor DNA according to the invention and as disclosed herein, wherein the kit further comprises at least two oligonucleotides for use in the method as described herein, preferably the at least two oligonucleotides as described herein.

In this embodiment, the kit may thus comprise at least a first and a second oligonucleotide that, independently, each comprise at least one domain that is capable of hybridizing to, respectively, the first or second DNA sequence and which domain comprises, or is directly adjacent to at least one mismatch with respect to, respectively, the first or second DNA sequence, and wherein said at least one mismatch is positioned at most 2, preferably at most 1 nucleotide from the 3' end of said oligonucleotide, most preferably said at least one mismatch is at the 3' end of the oligonucleotide, and wherein the mismatch in the first oligonucleotide and the mismatch in the second oligonucleotide each target a different nucleotide, wherein the nucleotide targeted in the first strand occupies the complementary position of the targeted nucleotide in the second strand, e.g. the nucleotides form a base-pair in the duplex DNA, and in addition comprises instructions to perform the method according to the invention.

As will be understood by the skilled person, by providing instructions at least informing that the above mismatch is positioned at the 3' end of the oligonucleotide(s) or 1 nucleotide from the 3' end or 2 nucleotides from the 3' end, and that the oligonucleotide(s) can be used for alteration of a duplex DNA sequence, such kit comprising these instructions and the oligonucleotide(s) are a kit within the scope of the above described and claimed kits.

The kit may, for example, also take the form of a website or a document providing instructions or information to perform targeted alteration of a duplex acceptor DNA according to the method of the invention, as described and disclosed herein, and the (separate) provision or offering of an oligonucleotide(s) suitable for use in the method according to the invention, and as described and disclosed herein.

In a preferred embodiment there is provided for a kit according to the invention, as described above, wherein the oligonucleotide is an oligonucleotide that, when combined with a duplex acceptor DNA sequence containing a first DNA sequence and a second DNA sequence which is the complement of the first DNA sequence, comprises a domain that is capable of hybridizing to the first DNA sequence, which domain comprises, or is directly adjacent to, at least one mismatch with respect to the first DNA sequence, and wherein said at least one mismatch is located at most 2, preferably at most 1 nucleotide from the 3' end of said oligonucleotide, most preferably said at least one mismatch is at the 3' end of the oligonucleotide.

In a preferred embodiment there is provided a kit wherein, when combined with a duplex acceptor DNA sequence containing a first DNA sequence and a second DNA sequence which is the complement of the first DNA sequence, the first oligonucleotide comprises at least one domain that is capable of hybridizing to the first DNA sequence and wherein the first oligonucleotide further comprises at least one mismatch with respect to the first DNA sequence and wherein the at least one mismatch is positioned at most 2 nucleotides from the 3' end of said first oligonucleotide; and wherein the second oligonucleotide comprises at least one domain that is capable of hybridizing to the second DNA sequence and wherein the second oligonucleotide further comprises at least one mismatch with respect to the second DNA sequence and wherein the at least one mismatch is positioned at most 2 nucleotides from the 3' end of said second oligonucleotide; and wherein the at least one mismatch in the first oligonucleotide is relative to a nucleotide in the first DNA sequence of the duplex acceptor DNA sequence and wherein the at least one mismatch in the second oligonucleotide is relative to a nucleotide in the second DNA sequence of the duplex acceptor DNA, and wherein said nucleotides occupy complementary positions in the duplex acceptor DNA (for example, form a base pair in the duplex acceptor DNA).

As will be understood by the skilled person, in a preferred embodiment, the mismatch in the first oligonucleotide and the mismatch in the second oligonucleotide, each directed to a different nucleotide in a (the same) base-pair in the duplex DNA, is preferably such that when both mismatches would be introduced in the duplex DNA, these are complementary to each other and may form a base-pair (A-T/C-G) in the duplex DNA in which they are introduced.

EXAMPLES

Example 1

TNE on a GFP Episome in Tobacco Protoplasts Using 2 Oligonucleotides

TNE involves the introduction of oligonucleotides into cells where they induce a mutation in the genomic target locus, driven by a mismatch nucleotide in the oligonucleotide.

In the experiments below accuracy and efficiency of TNE was determined by performing TNE on an episome (plasmid) which carries a non-functional Green fluorescent protein (GFP) containing an in frame stop codon. Two oligonucleotides were designed each carrying at the 3' end a mismatch nucleotide which could repair the stop codon in GFP. Co-transfection of the plasmid together with the two oligonucleotides restored GFP expression and activity which was, in the experiments below, scored at a single cell level 24 hours after protoplast transfection. This first example describes experiments performed in tobacco protoplasts.

Materials and Methods
Constructs

The functional GFP open reading frame was synthesized and the codon usage was optimized for use in the Solanaceae. A variant of GFP was produced with a nucleotide change at position 82 (G to T) as shown in FIG. 1. This resulted in the production of an in frame stop codon and the amino acid sequence of the resulting protein is shown in FIG. 2. The GFP ORF (GFP WT) and GFP variant with the stop codon (GFP-STOP) were cloned as XhoI-SacI fragments in the multiple cloning site of a pUC based vector containing the CaMV 35S promoter for gene expression in plant cells. This resulted in the constructs pKG7381 (GFP-WT) and pKG7384 (GFP-STOP). In addition, GFP is translationally fused to a 6×HIS tag and an NLS (sequence nuclear localization signal) to facilitate accumulation of GFP protein in the protoplast nucleus and thus improve our ability to score GFP positive cells. These constructs are shown in FIG. 3.

Oligonucleotides

The oligonucleotides to repair the stop codon in the GFP gene are shown in Table 1.

TABLE 1

Oligonucleotides used in this study. The mismatch nucleotide in ODM3 and ODM4 is underlined. The asterisks represent phosphorothioate (PS) linkages. The orientation of the oligonucleotide is given as sense (identical to the GFP coding sequence) or antisense (complementary to the GFP coding sequence). All oligonucleotides are shown in the 5'-3' orientation.

| Oligo | Sequence | Orientation |
| --- | --- | --- |
| ODM1 | G*T*T*C*TCGAGATGGTGAGCA AG*G*G*C*T (SEQ ID NO: 3) | Sense |
| ODM2 | G*C*A*C*CACCCCGGTGAACAG CT*C*C*T*A (SEQ ID NO: 4) | Antisense |
| ODM3 | G*T*T*C*TCGAGATGGTGAGCA AG*G*G*C*<u>G</u> (SEQ ID NO: 5) | Sense |
| ODM4 | G*C*A*C*CACCCCGGTGAACAG CT*C*C*T*<u>C</u> (SEQ ID NO: 6) | Antisense |

Isolation and Transfection of Tobacco Protoplasts

The source material for this example was tobacco in vitro shoot cultures, grown aseptically in glass jars (750 ml) in MS20 medium at a temperature of 25/20° C. (day/night) and a photon flux density of 80 µE·m$^{-2}$·s$^{-1}$ (photoperiod of 16/24 h). MS20 medium is basic Murashige and Skoog's medium (Murashige, T. and Skoog, F., *Physiologia Plantarum*, 15: 473-497, 1962) containing 2% (w/v) sucrose, no added hormones and 0.8% Difco agar. The shoots were subcultured every 3 weeks to fresh medium.

For the isolation of mesophyllprotoplasts, fully expanded leaves of 3-6 week old shoot cultures were harvested. The leaves are sliced into 1 mm thin strips, which were then transferred to large (100 mm×100 mm) Petri dishes containing 45 ml MDE basal medium for a preplasmolysis treatment of 30 min at room temperature. MDE basal medium contained 0.25 g KCl, 1.0 g MgSO$_4$.7H$_2$O, 0.136 g of KH$_2$PO$_4$, 2.5 g polyvinylpyrrolidone (MW 10,000), 6 mg naphthalene acetic acid and 2 mg 6-benzylaminopurine in a total volume of 900 ml. The osmolarity of the solution was adjusted to 600 mOsm·kg$^{-1}$ with sorbitol, the pH to 5.7.

After preplasmolysis, 5 ml of enzyme stock was added to each Petri dish. The enzyme stock consisted of 750 mg Cellulase Onozuka R10, 500 mg driselase and 250 mg macerozyme R10 per 100 ml (Duchefa B. V., Haarlem, The Netherlands, e.g. products C8001 & M8002), filtered over Whatman paper and filter-sterilized. The Petri dishes were sealed and incubated overnight in the dark at 25° C. without movement to digest the cell walls.

The protoplast suspension was then passed through 500 µm and 100 µm sieves into 250 ml Erlenmeyer flasks, mixed with an equal volume of KCl wash medium, and centrifuged in 50 ml tubes at 85×g for 10 min. KCl wash medium consisted of 2.0 g CaCl$_2$.2H$_2$O per liter and a sufficient quantity of KCl to bring the osmolarity to 540 mOsm·kg$^{-1}$.

The centrifugation step was repeated twice, first with the protoplasts resuspended in MLm wash medium, which is the macro-nutrients of MS medium (Murashige, T. and Skoog, F., *Physiologia Plantarum*, 15: 473-497, 1962) at half the normal concentration, 2.2 g of CaCl$_2$.2H$_2$O per liter and a quantity of mannitol to bring the osmolality to 540 mOsm·kg$^{-1}$, and finally with the protoplasts resuspended in MLs medium, which is MLm medium with mannitol replaced by sucrose.

The protoplasts were recovered from the floating band in sucrose medium and resuspended in an equal volume of KCl wash medium. Their densities were counted using a haemocytometer. Subsequently, the protoplasts were centrifuged again in 10 ml glass tubes at 85×g for 5 min and the pellets resuspended at a density of 1×10$^5$ protoplasts ml$^{-1}$ in electroporation medium.

Protoplast Electroporation

A BioRad Gene Pulser apparatus was used for electroporation. Using PHBS as an electroporation medium (10 mM Hepes, pH 7.2; 0.2 M mannitol, 150 mM NaCl; 5 mM CaCl2) and with a protoplast density in the electroporation mixture of ca. 1×10$^6$ per ml, the electroporation settings were 250V (625 V cm$^{-1}$) charge and 800 µF capacitance with a recovery time between pulse and cultivation of 10 minutes. For each electroporation ca. 2 µg total oligonucleotide and 20 µg KG7381 or KG7384 were used per 800 microliter electroporation.

After the electroporation treatment, the protoplasts were placed on ice for 30 min to recover, then resuspended in T$_0$ culture medium at a density of 1×10$^5$ protoplasts ml$^{-1}$ and incubated at 21° C. overnight in the dark. T$_0$ culture medium contained (per liter, pH 5.7) 950 mg KNO$_3$, 825 mg NH$_4$NO$_3$, 220 mg CaCl$_2$.2H$_2$O, 185 mg MgSO$_4$.7H$_2$O, 85 mg KH$_2$PO$_4$, 27.85 mg FeSO$_4$.7H$_2$O, 37.25 mg Na$_2$EDTA.2H$_2$O, the micro-nutrients according to Heller's medium (Heller, R., *Ann Sci Nat Bot Biol Veg* 14: 1-223, 1953), vitamins according to Morel and Wetmore's medium (Morel, G. and R. H. Wetmore, *Amer. J. Bot.* 38: 138-40, 1951), 2% (w/v) sucrose, 3 mg naphthalene acetic acid, 1 mg 6-benzylaminopurine and a quantity of mannitol to bring the osmolality to 540 mOsm·kg$^{-1}$ The protoplasts were examined under the UV microscope 20 hours after electroporation to visualize the GFP signal in the nucleus.

Alternatively, PEG treatment could be used to introduce the plasmid and oligonucleotide DNA into tobacco protoplasts. Methods to achieve this are well known in the literature.

Results

When the construct KG7381 (GFP-WT) was electroporated to tobacco protoplasts a strong GFP signal located in the nucleus after approximately 20 hours of incubation was observed. This signal is due to the strong transient expression of the GFP ORF. This signal disappeared within 48 hours, presumably due to degradation/elimination of the plasmid DNA from the cell. In a typical experiment, approximately 30% of the protoplasts showed a GFP signal and this represents the maximal electroporation efficiency. No GFP signal was observed when KG7384 (GFP-STOP) was introduced into tobacco protoplasts.

Once the experimental setup had been validated, experiments were performed whereby KG7384 was introduced into tobacco protoplasts in combination with the oligonucleotides described above. The GFP signal was scored after 24 hours and the results are shown in table 2.

TABLE 2

Repair of episomal GFP
Repair efficiency was calculated as the percentage of cells with restored GFP expression scored via fluorescence.

| Treatment | Oligonucleotide(s) | Repair efficiency (%) |
|---|---|---|
| 1 | ODM1 | 0 |
| 2 | ODM2 | 0 |
| 3 | ODM3 | 20 |
| 4 | ODM4 | 14 |
| 5 | ODM1 + ODM2 | 0 |
| 6 | ODM3 + ODM4 | 80 |

When oligonucleotides lacking a mismatch at the 3' end (ODM1 and ODM2) were added separately (treatment 1 & 2) or together (treatment 5) no restoration of GFP activity was observed. In contrast, we did observe restoration of GFP expression when oligonucleotides carrying a single mismatch at the 3' end (ODM3 and ODM4) were used (treatment 3 & 4). Surprisingly, we were able to demonstrate that the repair efficiency was higher than expected when ODM3 and ODM4 were added simultaneously. Therefore, such an approach appears to significantly improve the efficiency of TNE and enables the development of a more efficient TNE methodology.

Example 2

Effects of PS Linkage on TNE Efficiency

This example shows that it is not required that the first or the second oligonucleotide according to the invention incorporates nucleotides having e.g. phosphorothioate linkages nor that is it required that any other type of modification is incorporated.

Methods

Tomato mesophyllprotoplasts were isolated from young leaves of tomato in vitro plants. Reporter constructs harbouring an eYFP (stop) gene (see FIGS. 5 and 6) whose expression was driven by the CaMV 35S promoter and oligonucleotides were transfected into tomato protoplasts by a PEG-mediated method. After overnight incubation under dark at 30° C. in a growth chamber, infected protoplasts were observed using a fluorescent microscope equipped with a YFP filter set. The number of protoplasts emitting yellow fluorescence was scored and the TNE efficiency was calculated by dividing the number of yellow protoplasts by the number of transfected protoplasts.

Sequence of Oligonucleotides Tested:

PB72
(SEQ ID NO: 7)
C*A*T*G*CATGCATGCATGCATGC*A*T*G*C
25 mer, PS, Nonsense (=negative control)

Figure 4:
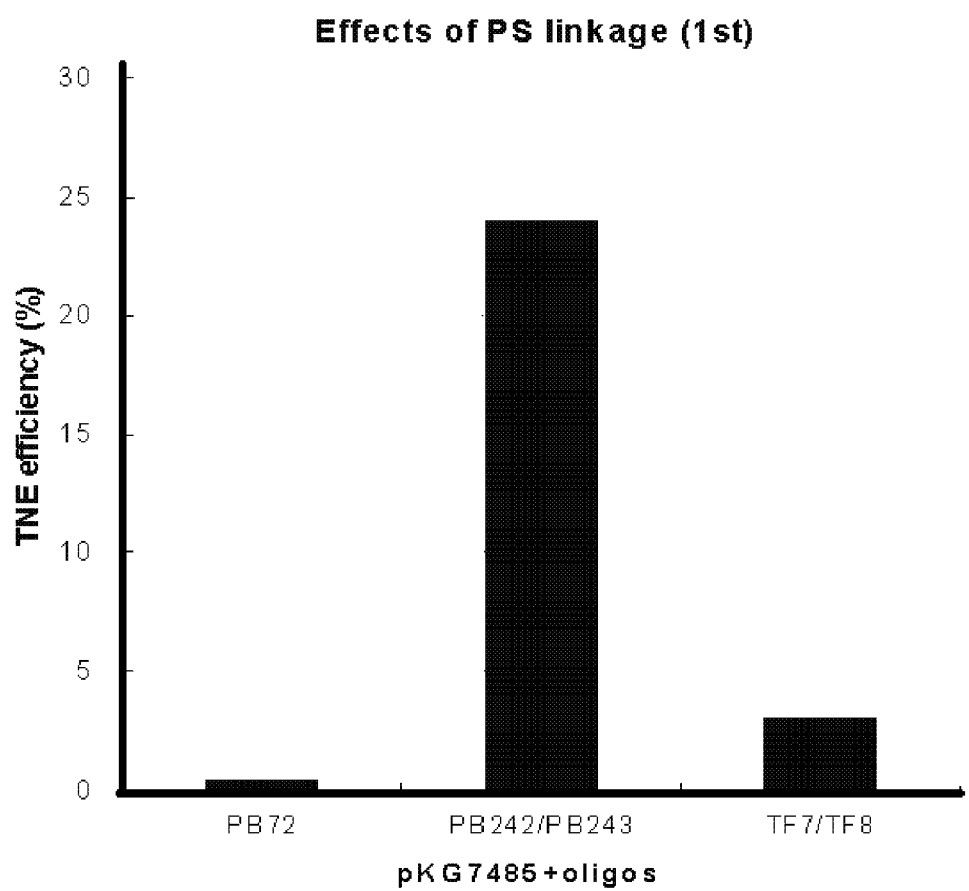
FIG. 4 Data showing TNE efficiency with oligonucleotides according to the invention.

PB242
(SEQ ID NO: 8)
T*G*A*G*GGTGAAGGTGATGCTAC*T*T*A*C
25 mer, PS, 3' MM (=mismatch) Sense PB243
(SEQ ID NO: 9)
G*A*T*G*AACTTAAGTGTAAGTTT*A*C*C*G
25 mer, PS, 3' MM Antisense TF7
(SEQ ID NO: 10)
TGAGGGTGAAGGTGATGCTACTTAC
25 mer, 3' MM Sense TF8
(SEQ ID NO: 11)
GATGAACTTAAGTGTAAGTTTACCG
25 mer, 3' MM Antisense
*represents a phosphorothioate linkage The TNE reaction caused by PB242, PB243, TF7, and TF8 converts the target sequence from TAA to TAC. Oligonucleotides PB242, PB243, TF7 and TF8 were thus designed to repair the STOP codon in YFP, wherein PB72, PB242, and PB243 comprise PS linkages, and TF7 and TF8 do not comprise PS linkages. As shown in FIG. 4, PB242+ PB243 was able to restore YFP expression with more than 23%; TF7+TF8 was able to restore YFP expression with more than 3%, almost 10 times more in comparison to the signal obtained with the nonsense oligonucleotide.

This example thus shows that using oligonucleotides, with or without modification, like PS linkages, can be used in TNE.

LITERATURE

Alexeev, V. and Yoon, K. (1998). Stable and inheritable changes in genotype and phenotype of albino melanocytes induced by an RNA-DNA oligonucleotide. *Nat Biotechnol* 16, 1343-6.

Beetham, P. R., Kipp, P. B., Sawycky, X. L., Arntzen, C. J. and May, G. D. (1999). A tool for functional plant genomics: chimeric RNA/DNA oligonucleotides cause in vivo gene-specific mutations. *Proc Natl Acad Sci USA* 96, 8774-8.

Dong, C., Beetham, P., Vincent, K. and Sharp, P. (2006). Oligonucleotide-directed gene repair in wheat using a transient plasmid gene repair assay system. *Plant Cell Rep* 25, 457-65.

Igoucheva, O., Alexeev, V. and Yoon, K. (2001). Targeted gene correction by small single-stranded oligonucleotides in mammalian cells. *Gene Ther* 8, 391-9.

Kmiec, E. B. (2003). Targeted gene repair—in the arena. *J Clin Invest* 112, 632-6.

Kochevenko, A. and Willmitzer, L. (2003). Chimeric RNA/ DNA oligonucleotide-based site-specific modification of the tobacco acetolactate syntase gene. *Plant Physiol* 132, 174-84.

Liu, L., Cheng, S., van Brabant, A. J. and Kmiec, E. B. (2002). Rad51p and Rad54p, but not Rad52p, elevate gene repair in *Saccharomyces cerevisiae* directed by modified single-stranded oligonucleotide vectors. *Nucleic Acids Res* 30, 2742-50.

Okuzaki, A. and Toriyama, K. (2004). Chimeric RNA/DNA oligonucleotide-directed gene targeting in rice. *Plant Cell Rep* 22, 509-12.

Parekh-Olmedo, H., Ferrara, L., Brachman, E. and Kmiec, E. B. (2005). Gene therapy progress and prospects: targeted gene repair. *Gene Ther* 12, 639-46.

Rice, M. C., Czymmek, K. and Kmiec, E. B. (2001). The potential of nucleic acid repair in functional genomics. *Nat Biotechnol* 19, 321-6.

Ruiter, R., van den Brande, I., Stals, E., Delaure, S., Cornelissen, M. and D'Halluin, K. (2003). Spontaneous mutation frequency in plants obscures the effect of chimeraplasty. *Plant Mol Biol* 53, 675-89.

Zhu, T., Mettenburg, K., Peterson, D. J., Tagliani, L. and Baszczynski, C. L. (2000). Engineering herbicide-resistant maize using chimeric RNA/DNA oligonucleotides. *Nat Biotechnol* 18, 555-8.

Zhu, T., Peterson, D. J., Tagliani, L., St Clair, G., Baszczynski, C. L. and Bowen, B. (1999). Targeted manipulation of maize genes in vivo using chimeric RNA/DNA oligonucleotides. *Proc Natl Acad Sci USA* 96, 8768-73.

The invention claimed is:

1. A method for targeted alteration of a duplex acceptor DNA sequence comprising the step of
combining the duplex acceptor DNA sequence with at least a first oligonucleotide and a second oligonucleotide, wherein the duplex acceptor DNA sequence comprises a first DNA sequence and a second DNA sequence, which is complementary to the first DNA sequence; and
wherein the first oligonucleotide comprises at least one domain that is capable of hybridizing to the first DNA sequence and wherein the first oligonucleotide further comprises at least one mismatch with respect to the first DNA sequence and wherein this at least one mismatch is positioned at most 2 nucleotides from the 3' end of said first oligonucleotide;
and wherein the second oligonucleotide comprises at least one domain that is capable of hybridizing to the second DNA sequence and wherein the second oligonucleotide further comprises at least one mismatch with respect to the second DNA sequence and wherein this at least one mismatch is positioned at most 2 nucleotides from the 3' end of said second oligonucleotide;
and wherein the at least one mismatch in the first oligonucleotide is relative to a nucleotide in the first DNA sequence of the duplex acceptor DNA sequence and wherein the at least one mismatch in the second oligonucleotide is relative to a nucleotide in the second DNA sequence of the duplex acceptor DNA sequence, and wherein said nucleotide in the first DNA sequence and said nucleotide in the second DNA sequence occupy complementary positions in the duplex acceptor DNA sequence;
and wherein the alteration of the duplex acceptor DNA sequence is within a cell.

2. The method according to claim 1, wherein the mismatch in the first oligonucleotide is positioned at most 1 nucleotide from the 3' end of said first oligonucleotide and, independently, the mismatch in the second oligonucleotide is positioned at most 1 nucleotide from the 3' end of said second oligonucleotide.

3. The method according to claim 1, wherein the domain in the first oligonucleotide comprises or is directly adjacent to the at least one mismatch in the first oligonucleotide and/or the domain in the second oligonucleotide comprises or is directly adjacent to the at least one mismatch in the second oligonucleotide.

4. The method according to claim 1, wherein the first oligonucleotide is complementary to the first DNA sequence except for the one mismatch and/or wherein the second oligonucleotide is complementary to the second DNA sequence except for the one mismatch.

5. The method according to claim 4, wherein the mismatch in the first oligonucleotide is at the 3' end and wherein the mismatch in the second oligonucleotide is at the 3' end.

6. The method according to claim 1, wherein the first oligonucleotide comprises at least one section that contains at least one modified nucleotide and/or the second oligonucleotide comprises at least one section that contains at least one modified nucleotide, wherein each said modified nucleotide contains a modification that is independently selected from the group consisting of a base modification, a backbone modification or a sugar modification.

7. The method according to claim 6, wherein each said modified nucleotide is independently selected from the group consisting of Locked Nucleic Acids (LNA) or phosphorothioate bonds.

8. The method according to claim 6, wherein the first oligonucleotide and/or the second oligonucleotide comprises at least two modified nucleotides.

9. The method according to claim 1, wherein the at least one mismatch in the first oligonucleotide and the at least one mismatch in the second oligonucleotide are not modified nucleotides.

10. The method according to claim 6, wherein the at least one modified nucleotide is at least one nucleotide from the at least one mismatch, and wherein the at least one mismatch is located at most 2 nucleotides from the 3' end of said oligonucleotide.

11. The method according to claim 1, wherein the alteration of the duplex acceptor DNA sequence is within a cell selected from the group consisting of a prokaryotic cell, a bacterial cell, a eukaryotic cell, a plant cell, an animal cell, a yeast cell, a fungal cell, a rodent cell, a human cell, a non-human cell, and an embryonic cell.

12. The method according to claim 1, wherein the duplex acceptor DNA sequence is from a prokaryotic organism, a bacterium, an eukaryotic organism, a plant, an animal, a yeast, a fungus, a rodent, or a human.

13. The method according to claim 1, wherein the alteration is a deletion, a substitution and/or an insertion of at least one nucleotide.

14. The method according to claim 1, wherein the duplex acceptor DNA sequence is from genomic DNA, linear DNA, artificial chromosomes, mammalian artificial chromosomes, bacterial artificial chromosomes, yeast artificial chromosomes, plant artificial chromosomes, nuclear chromosomal DNA, organellar DNA, plasmid DNA or episomal DNA.

15. The method according to claim 1, wherein the method is useful for altering a cell, correcting a mutation by restoration to wild type, inducing a mutation, inactivating an enzyme by disruption of coding region, modifying bioactivity of an enzyme by altering coding region, modifying a protein by disrupting the coding region, mismatch repair, targeted alteration of plant genetic material, including gene mutation, targeted gene repair and gene knockout.

16. The method according to claim 2, wherein the mismatch in the first oligonucleotide is positioned at the 3' end of said first oligonucleotide or the mismatch in the second oligonucleotide is positioned at the 3' end of said second oligonucleotide.

17. The method according to claim 2, wherein the mismatch in the first oligonucleotide is positioned at the 3' end of said first oligonucleotide and the mismatch in the second oligonucleotide is positioned at the 3' end of said second oligonucleotide.

18. The method according to claim 6, wherein at least one modified nucleotide contains a base modification, wherein said base modification is a 3' or 5' end base modification.

19. The method according to claim 8, wherein the first oligonucleotide and/or the second oligonucleotide comprises at least three modified nucleotides.

20. The method according to claim 8, wherein the first oligonucleotide and/or the second oligonucleotide comprises at least four modified nucleotides.

21. The method according to claim 8, wherein the first oligonucleotide and/or the second oligonucleotide comprises at least five modified nucleotides.

22. The method according to claim 8, wherein the first oligonucleotide and/or the second oligonucleotide comprises three modified nucleotides.

23. The method according to claim 8, wherein the first oligonucleotide and/or the second oligonucleotide comprises two, three, four, or five modified nucleotides.

24. The method according to claim 10, wherein the at least one mismatch is located at most 1 nucleotide from the 3' end of said oligonucleotide.

25. The method according to claim 10, wherein the at least one mismatch is located at the 3' end of said oligonucleotide.

* * * * *

SEQUENCE LISTING

```
<160> NUMBER OF SEQ ID NOS: 13

<210> SEQ ID NO 1
<211> LENGTH: 786
<212> TYPE: DNA
<213> ORGANISM: Artificial Sequence
<220> FEATURE:
<223> OTHER INFORMATION: GFP ORF containing a stop codon

<400> SEQUENCE: 1
atgggaagag gatcgcatca ccaccatcat cataagcttc caaagaagaa gaggaaggtt      60
ctcgagatgg tgagcaaggg ctaggagctg ttcaccgggg tggtgcccat cctggtcgag     120
ctggacggcg acgtaaacgg ccacaagttc agcgtgtccg gcgagggcga gggcgatgcc     180
acctacggca agctgaccct gaagttcatc tgcaccaccg gcaagctgcc cgtgccctgg     240
cccaccctcg tgaccaccct gacctacggc gtgcagtgct tcagccgcta ccccgaccac     300
atgaagcagc acgacttctt caagtccgcc atgcccgaag gctacgtcca ggagcgcacc     360
atcttcttca aggacgacgg caactacaag acccgcgccg aggtgaagtt cgagggcgac     420
accctggtga accgcatcga gctgaagggc atcgacttca aggaggacgg caacatcctg     480
gggcacaagc tggagtacaa ctacaacagc cacaacgtct atatcatggc cgacaagcag     540
aagaacggca tcaaggtgaa cttcaagatc cgccacaaca tcgaggacgg cagcgtgcag     600
ctcgccgacc actaccagca gaacacccccc atcggcgacg gccccgtgct gctgcccgac     660
aaccactacc tgagcaccca gtccgccctg agcaaagacc ccaacgagaa gcgcgatcac     720
atggtcctgc tggagttcgt gaccgccgcc gggatcactc tcggcatgga cgagctgtac     780
aagtaa                                                                786

<210> SEQ ID NO 2
<211> LENGTH: 260
<212> TYPE: PRT
<213> ORGANISM: Artificial Sequence
<220> FEATURE:
<223> OTHER INFORMATION: GFP-STOP protein

<400> SEQUENCE: 2

Met Gly Arg Gly Ser His His His His His Lys Leu Pro Lys Lys
1               5                   10                  15

Lys Arg Lys Val Leu Glu Met Val Ser Lys Gly Glu Leu Phe Thr Gly
            20                  25                  30

Val Val Pro Ile Leu Val Glu Leu Asp Gly Asp Val Asn Gly His Lys
        35                  40                  45

Phe Ser Val Ser Gly Glu Gly Glu Gly Asp Ala Thr Tyr Gly Lys Leu
    50                  55                  60

Thr Leu Lys Phe Ile Cys Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
```

```
                            85                  90                  95
Pro Asp His Met Lys Gln His Asp Phe Phe Lys Ser Ala Met Pro Glu
                    100                 105                 110
Gly Tyr Val Gln Glu Arg Thr Ile Phe Phe Lys Asp Asp Gly Asn Tyr
                115                 120                 125
Lys Thr Arg Ala Glu Val Lys Phe Glu Gly Asp Thr Leu Val Asn Arg
            130                 135                 140
Ile Glu Leu Lys Gly Ile Asp Phe Lys Glu Asp Gly Asn Ile Leu Gly
145                 150                 155                 160
His Lys Leu Glu Tyr Asn Tyr Asn Ser His Asn Val Tyr Ile Met Ala
                165                 170                 175
Asp Lys Gln Lys Asn Gly Ile Lys Val Asn Phe Lys Ile Arg His Asn
                180                 185                 190
Ile Glu Asp Gly Ser Val Gln Leu Ala Asp His Tyr Gln Gln Asn Thr
                195                 200                 205
Pro Ile Gly Asp Gly Pro Val Leu Leu Pro Asp Asn His Tyr Leu Ser
            210                 215                 220
Thr Gln Ser Ala Leu Ser Lys Asp Pro Asn Glu Lys Arg Asp His Met
225                 230                 235                 240
Val Leu Leu Glu Phe Val Thr Ala Ala Gly Ile Thr Leu Gly Met Asp
                245                 250                 255
Glu Leu Tyr Lys
        260

<210> SEQ ID NO 3
<211> LENGTH: 25
<212> TYPE: DNA
<213> ORGANISM: Artificial Sequence
<220> FEATURE:
<223> OTHER INFORMATION: oligonucleotide

<400> SEQUENCE: 3
gttctcgaga tggtgagcaa gggct                                        25

<210> SEQ ID NO 4
<211> LENGTH: 25
<212> TYPE: DNA
<213> ORGANISM: Artificial Sequence
<220> FEATURE:
<223> OTHER INFORMATION: oligonucleotide

<400> SEQUENCE: 4
gcaccacccc ggtgaacagc tccta                                        25

<210> SEQ ID NO 5
<211> LENGTH: 25
<212> TYPE: DNA
<213> ORGANISM: Artificial Sequence
<220> FEATURE:
<223> OTHER INFORMATION: oligonucleotide

<400> SEQUENCE: 5
gttctcgaga tggtgagcaa gggcg                                        25

<210> SEQ ID NO 6
<211> LENGTH: 25
<212> TYPE: DNA
<213> ORGANISM: Artificial Sequence
<220> FEATURE:
<223> OTHER INFORMATION: oligonucleotide
```

```
<400> SEQUENCE: 6
gcaccacccc ggtgaacagc tcctc                                          25

<210> SEQ ID NO 7
<211> LENGTH: 25
<212> TYPE: DNA
<213> ORGANISM: Artificial Sequence
<220> FEATURE:
<223> OTHER INFORMATION: oligonucleotide

<400> SEQUENCE: 7
catgcatgca tgcatgcatg catgc                                          25

<210> SEQ ID NO 8
<211> LENGTH: 25
<212> TYPE: DNA
<213> ORGANISM: Artificial Sequence
<220> FEATURE:
<223> OTHER INFORMATION: oligonucleotide

<400> SEQUENCE: 8
tgagggtgaa ggtgatgcta cttac                                          25

<210> SEQ ID NO 9
<211> LENGTH: 25
<212> TYPE: DNA
<213> ORGANISM: Artificial Sequence
<220> FEATURE:
<223> OTHER INFORMATION: oligonucleotide

<400> SEQUENCE: 9
gatgaactta agtgtaagtt taccg                                          25

<210> SEQ ID NO 10
<211> LENGTH: 25
<212> TYPE: DNA
<213> ORGANISM: Artificial Sequence
<220> FEATURE:
<223> OTHER INFORMATION: oligonucleotide

<400> SEQUENCE: 10
tgagggtgaa ggtgatgcta cttac                                          25

<210> SEQ ID NO 11
<211> LENGTH: 25
<212> TYPE: DNA
<213> ORGANISM: Artificial Sequence
<220> FEATURE:
<223> OTHER INFORMATION: oligonucleotide

<400> SEQUENCE: 11
gatgaactta agtgtaagtt taccg                                          25

<210> SEQ ID NO 12
<211> LENGTH: 786
<212> TYPE: DNA
<213> ORGANISM: Artificial Sequence
<220> FEATURE:
<223> OTHER INFORMATION: YFP-STOP

<400> SEQUENCE: 12
atgggaagag gatcgcatca ccaccatcat cataagcttc caaagaagaa gaggaaggtt    60
ctcgagatgg tttctaaggg tgaggaactt ttcactggtg tggttccaat tctcgttgag   120
cttgatggtg atgttaacgg acacaagttc tctgtttctg gtgaaggtga aggtgatgct   180
```

```
acttaaggaa agcttactct caagttcatc tgcactactg gaaagcttcc agttccatgg        240
ccaactcttg ttactacttt cggatacggt gttcaatgct tcgctaggta tccagatcat        300
atgaggcagc acgatttctt caagtctgct atgccagagg gatatgttca agagaggact        360
atcttcttca aggatgatgg caactacaag actagggctg aggttaagtt cgagggtgat        420
actcttgtga acaggattga gcttaagggc atcgatttca agaggatgg aaacattctc         480 ggccacaagc ttgagtacaa ctacaattct cacaacgtgt acatcatggc tgataagcag        540
aagaacggca tcaaggttaa cttcaagatc aggcacaaca tcgaggatgg atctgttcaa        600
cttgctgatc attaccagca gaacactcca attggagatg gaccagttct tcttcctgat        660
aaccactacc tttcttacca gtctgctctt tccaaggatc caaatgagaa gagggatcac        720
atggtgcttt ggagtttgt tactgctgct ggaatcactc ttggcatgga tgaactctac         780
aagtga                                                                   786
```

```
<210> SEQ ID NO 13
<211> LENGTH: 261
<212> TYPE: PRT
<213> ORGANISM: Artificial Sequence
<220> FEATURE:
<223> OTHER INFORMATION: YFP-STOP

<400> SEQUENCE: 13

Met Gly Arg Gly Ser His His His His His Lys Leu Pro Lys Lys
1               5                   10                  15

Lys Arg Lys Val Tyr Leu Glu Met Val Ser Lys Gly Glu Glu Leu Phe
            20                  25                  30

Thr Gly Val Val Pro Ile Leu Val Glu Leu Asp Gly Asp Val Asn Gly
        35                  40                  45

His Lys Phe Ser Val Ser Gly Glu Gly Glu Gly Asp Ala Thr Gly Lys
    50                  55                  60

Leu Thr Leu Lys Phe Ile Cys Thr Thr Gly Lys Leu Pro Val Pro Trp
65                  70                  75                  80

Pro Thr Leu Val Thr Thr Phe Gly Tyr Gly Val Gln Cys Phe Ala Arg
                85                  90                  95

Tyr Pro Asp His Met Arg Gln His Asp Phe Phe Lys Ser Ala Met Pro
            100                 105                 110

Glu Gly Tyr Val Gln Glu Arg Thr Ile Phe Phe Lys Asp Asp Gly Asn
        115                 120                 125

Tyr Lys Thr Arg Ala Glu Val Lys Phe Glu Gly Asp Thr Leu Val Asn
    130                 135                 140

Arg Ile Glu Leu Lys Gly Ile Asp Phe Lys Glu Asp Gly Asn Ile Leu
145                 150                 155                 160

Gly His Lys Leu Glu Tyr Asn Tyr Asn Ser His Asn Val Tyr Ile Met
                165                 170                 175

Ala Asp Lys Gln Lys Asn Gly Ile Lys Val Asn Phe Lys Ile Arg His
            180                 185                 190

Asn Ile Glu Asp Gly Ser Val Gln Leu Ala Asp His Tyr Gln Gln Asn
        195                 200                 205

Thr Pro Ile Gly Asp Gly Pro Val Leu Leu Pro Asp Asn His Tyr Leu
    210                 215                 220
```

-continued

```
Ser Tyr Gln Ser Ala Leu Ser Lys Asp Pro Asn Glu Lys Arg Asp His
225                 230                 235                 240

Met Val Leu Leu Glu Phe Val Thr Ala Ala Gly Ile Thr Leu Gly Met
            245                 250                 255

Asp Glu Leu Tyr Lys
            260
```